United States Patent
Benner et al.

(10) Patent No.: US 9,637,783 B1
(45) Date of Patent: May 2, 2017

(54) AMPLIFICATION OF OLIGONUCLEOTIDES CONTAINING NON-STANDARD NUCLEOTIDES BY POLYMERASE CHAIN REACTIONS

(71) Applicants: Steven Benner, Gainesville, FL (US); Roberto Laos, Gainesville, FL (US); Nicole Leal, Gainesville, FL (US); Nilesh Karalkar, Gainesville, FL (US); Zunyi Yang, Gainesville, FL (US)

(72) Inventors: Steven Benner, Gainesville, FL (US); Roberto Laos, Gainesville, FL (US); Nicole Leal, Gainesville, FL (US); Nilesh Karalkar, Gainesville, FL (US); Zunyi Yang, Gainesville, FL (US)

( * ) Notice: Subject to any disclaimer, the term of this patent is extended or adjusted under 35 U.S.C. 154(b) by 0 days.

(21) Appl. No.: 14/746,243

(22) Filed: Jun. 22, 2015

Related U.S. Application Data

(63) Continuation-in-part of application No. 14/082,800, filed on Nov. 18, 2013, which is a continuation-in-part of application No. 13/493,172, filed on Jun. 11, 2012, now Pat. No. 8,586,303, which is a continuation-in-part of application No. 12/999,138, filed as application No. PCT/US2009/003595 on Jun. 16, 2009, now Pat. No. 8,614,072, application No. 14/746,243, which is a continuation-in-part of application No. 14/138,532, filed on Jan. 15, 2014, now Pat. No. 9,062,345, which is a continuation-in-part of application No. 12/999,138, filed on Dec. 15, 2010, now Pat. No. 8,614,072.

(60) Provisional application No. 61/132,225, filed on Jun. 17, 2008.

(51) Int. Cl.
*C12Q 1/68* (2006.01)
*C12P 19/34* (2006.01)
*C12N 9/12* (2006.01)

(52) U.S. Cl.
CPC ......... *C12Q 1/6869* (2013.01); *C12N 9/1252* (2013.01); *C12P 19/34* (2013.01); *C12Q 2525/117* (2013.01); *C12Y 207/07007* (2013.01)

(58) Field of Classification Search
CPC ....................... C12Q 1/6869; C12Q 2525/117
USPC ........................................................ 435/6.1
See application file for complete search history.

(56) References Cited

U.S. PATENT DOCUMENTS

| 5,432,272 A | 7/1995 | Benenr |
| 8,354,225 B1 | 1/2013 | Benner |
| 8,586,303 B1 | 11/2013 | Benner |
| 2004/0106108 A1* | 6/2004 | Grenier ................ C12Q 1/6823 435/6.18 |

OTHER PUBLICATIONS

Johnson SC. et al. (2004) A third base pair for the polymerase chain reaction: inserting isoC and isoG. Nucl. Acids Res. 32, 1937-1941.

(Continued)

*Primary Examiner* — Jezia Riley

(57) ABSTRACT

This invention relates to processes that amplify, in a polymerase chain reaction architecture, oligonucleotide analogs that incorporate non-standard nucleobase analogs from an artificially expanded genetic information system. These pair in DNA duplexes via patterns of hydrogen bonds that are different from patterns that join the thymine-adenine and guanine-cytosine nucleobase pairs.

26 Claims, 19 Drawing Sheets

(56) References Cited

OTHER PUBLICATIONS

Bain JD. et al (1992) Ribosome-mediated incorporation of non-standard amino acids into a peptide through expansion of the genetic code. Nature 356. 537-539.

Horlacher J. et al. (1995) Expanding the genetic alphabet: Recognition by viral and cellular DNA polymerases of nucleosides bearing bases with non-standard hydrogen bonding patterns. Proc. Natl. Acad. Sci. 92. 6329-6333.

Him HJ. et al Kim, H. J., Leal, N. A., Benner. S. A. (2009) 2'-Deoxy-1-methylpseudocytidine. A Stable analog of 2'-deoxy-5-methylisocytidine. Bioorg. Med. Chem. 17, 3728-3732.

Hirama, Y. et al (2011) Synthesis and characterization of oligodeoxynucleotides containing a novel tetraazabenzo[cd] azulene:naphathyridine base pair, Bioorgan & Medic Chem 19, 352-358.

Seela, F. Regioselective syntheses of 7-halogenated 7-deazapurine nucleosides related to 2-amino-7-deaza-2'-deoxyadenosine and 7-deaza-2'deoxyisoguanosine. Syntheses, 8, 1203-1210.

* cited by examiner

SEQUENCE LISTING

<160> NUMBER OF SEQ ID NOS: 66

<210> SEQ ID NO 1
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: n = misc_structure
<222> LOCATION: (4)..(4)
<223> OTHER INFORMATION: 2,4-diamino-5-(1'-beta-D-2'-
     deoxyribofuranosyl)-pyrimidine
<220> FEATURE:
<221> NAME/KEY: misc_feature
<222> LOCATION: (4)..(4)
<223> OTHER INFORMATION: n is a, c, g, t or u

```
<220> FEATURE:
<221> NAME/KEY: n = misc_structure
<222> LOCATION: (8)..(8)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: n = misc_structure
<222> LOCATION: (12)..(12)
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: n = misc_structure
<222> LOCATION: (16)..(16)
<220> FEATURE:
<221> NAME/KEY: misc_feature
<222> LOCATION: (16)..(16)
<223> OTHER INFORMATION: n is a, c, g, t or u

<400> SEQUENCE: 1
ctangacnac gnactnc                                                    17

<210> SEQ ID NO 2
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: n = misc_structure
<222> LOCATION: (4)..(4)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: n = misc_structure
<222> LOCATION: (8)..(8)
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: n = misc_structure
<222> LOCATION: (12)..(12)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: n = misc_structure
<222> LOCATION: (16)..(16)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (16)..(16)
<223> OTHER INFORMATION: n is a, c, g, t or u

<400> SEQUENCE: 2
cagnaagnag cnatcnc                                                    17

<210> SEQ ID NO 3
<211> LENGTH: 59
<212> TYPE: DNA
<213> ORGANISM: Artificial Sequence
```

```
<220> FEATURE:
<223> OTHER INFORMATION: Synthetic
<220> FEATURE:
<221> NAME/KEY: n = misc_structure
<222> LOCATION: (4)..(4)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: n = misc_structure
<222> LOCATION: (8)..(8)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: n = misc_structure
<222> LOCATION: (12)..(12)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: n = misc_structure
<222> LOCATION: (16)..(16)
<223> OTHER INFORMATION: 2,4-diamino-5-(1'-beta-D-2'-
      deoxyribofuranosyl)-pyrimidine
<220> FEATURE:
<221> NAME/KEY: misc_feature
<222> LOCATION: (16)..(16)
<223> OTHER INFORMATION: n is a, c, g, t or u

<400> SEQUENCE: 3
ctangacnac gnactnccac caggaagcag ccatcacaca cagtgcgcat cctgactgc      59

<210> SEQ ID NO 4
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: n = misc_structure
<222> LOCATION: (4)..(4)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (4)..(4)
<223> OTHER INFORMATION: n is a, c, g, t or u
<220> FEATURE:
<221> NAME/KEY: n = misc_structure
<222> LOCATION: (8)..(8)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (8)..(8)
<223> OTHER INFORMATION: n is a, c, g, t or u
<220> FEATURE:
<221> NAME/KEY: n = misc_structure
<222> LOCATION: (12)..(12)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (12)..(12)
<223> OTHER INFORMATION: n is a, c, g, t or u
```

```
<220> FEATURE:
<221> NAME/KEY: n = misc_structure
<222> LOCATION: (16)..(16)
<223> OTHER INFORMATION: 8-(beta-D-2'-deoxyribofuranosyl)imidazo[1,2-a]-
      1,3,5-triazine-2(8H)-4(3H)-dione
<220> FEATURE:
<221> NAME/KEY: misc_feature
<222> LOCATION: (16)..(16)
<223> OTHER INFORMATION: n is a, c, g, t or u

<400> SEQUENCE: 4
cagnaagnag cnatcnccac caggaagcag ccatcacaca cccaaggggt tatgctaggg     60

<210> SEQ ID NO 5
<211> LENGTH: 60
<212> TYPE: DNA
<213> ORGANISM: Artificial Sequence
<220> FEATURE:
<223> OTHER INFORMATION: Synthetic

<400> SEQUENCE: 5
gcgtaatacg actcactata gacgagctag atctcgagtc tttagtgagg gttaattcgc     60

<210> SEQ ID NO 6
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (34)..(34)
<223> OTHER INFORMATION: 2-amino-5-methyl-1-(1'-beta-D-2'-
      deoxyribofuranosyl)-4(1H)-pyrimidinone
<220> FEATURE:
<221> NAME/KEY: misc_feature
<222> LOCATION: (34)..(34)
<223> OTHER INFORMATION: n is a, c, g, t or u

<400> SEQUENCE: 6
gcgtaatacg actcactata gacgagctag atcncgagtc tttagtgagg gttaattcgc     60

<210> SEQ ID NO 7
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (34)..(34)
<223> OTHER INFORMATION: 5(N)-methyl-6-amino-3-(1'-beta-D-2'-
      deoxyribofuranosyl)-pyrimidin-2-one
<220> FEATURE:
<221> NAME/KEY: misc_feature
<222> LOCATION: (34)..(34)
<223> OTHER INFORMATION: n is a, c, g, t or u

<400> SEQUENCE: 7
gcgtaatacg actcactata gacgagctag atcncgagtc tttagtgagg gttaattcgc     60

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gcgtaatacg actcactata g                                              21
```

```
<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gcgaattaac cctcactaaa g                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gcgaattaac cctcactaaa g                                              21

<210> SEQ ID NO 11
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: N = misc_feature
<222> LOCATION: (26)..(27)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (26)..(27)
<223> OTHER INFORMATION: n is a, c, g, t or u

<400> SEQUENCE: 11
gcgtaatacg actcactata gacganncta ctttagtgag ggttaattcg c             51

<210> SEQ ID NO 12
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: z = misc_feature
<222> LOCATION: (25)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (25)..(26)
<223> OTHER INFORMATION: n is a, c, g, t or u

<400> SEQUENCE: 12
gcgaattaac cctcactaaa gtagnntcgt ctatagtgag tcgtattacg c             51

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gcgtaatacg actcactata g                                              21
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
gcgaattaac cctcactaaa g                                              21

<210> SEQ ID NO 15
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (27)..(29)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (27)..(29)
<223> OTHER INFORMATION: n is a, c, g, t or u

<400> SEQUENCE: 15
gcgtaatacg actcactata gacactnnnt actcacttta gtgagggtta attcgc        56

<210> SEQ ID NO 16
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: n= misc_feature
<222> LOCATION: (28)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(30)
<223> OTHER INFORMATION: n is a, c, g, t or u

<400> SEQUENCE: 16
gcgaattaac cctcactaaa gtgagtannn agtgtctata gtgagtcgta ttacgc        56

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
gcgtaatacg actcactata g                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
gcgaattaac cctcactaaa g                                              21
```

```
<210> SEQ ID NO 19
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (27)..(30)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (27)..(30)
<223> OTHER INFORMATION: n is a, c, g, t or u

<400> SEQUENCE: 19
gcgtaatacg actcactata gacactnnnn tactcacttt agtgagggtt aattcgc        57

<210> SEQ ID NO 20
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (28)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(31)
<223> OTHER INFORMATION: n is a, c, g, t or u

<400> SEQUENCE: 20
gcgaattaac cctcactaaa gtgagtannn nagtgtctat agtgagtcgt attacgc        57

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
gcgtaatacg actcactata g                                               21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
gcgtaatacg actcactata g                                               21

<210> SEQ ID NO 23
<211> LENGTH: 51
<212> TYPE: DNA
<213> ORGANISM: Artificial Sequence
<220> FEATURE:
<223> OTHER INFORMATION: Synthetic

<400> SEQUENCE: 23
gcgtaatacg actcactata gacgaggcta ctttagtgag ggttaattcg c              51
```

```
<210> SEQ ID NO 24
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (26)..(26)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (26)..(26)
<223> OTHER INFORMATION: n is a, c, g, t or u

<400> SEQUENCE: 24
gcgtaatacg actcactata gacgancgta ctttagtgag ggttaattcg c          51

<210> SEQ ID NO 25
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (26)..(27)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (26)..(27)
<223> OTHER INFORMATION: n is a, c, g, t or u

<400> SEQUENCE: 25
gcgtaatacg actcactata gacganncta ctttagtgag ggttaattcg c          51

<210> SEQ ID NO 26
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (27)..(29)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (27)..(29)
<223> OTHER INFORMATION: n is a, c, g, t or u

<400> SEQUENCE: 26
gcgtaatacg actcactata gacactnnnt actcacttta gtgagggtta attcgc     56

<210> SEQ ID NO 27
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (27)..(30)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (27)..(30)
<223> OTHER INFORMATION: n is a, c, g, t or u
```

<400> SEQUENCE: 27
gcgtaatacg actcactata gacactnnnn tactcactttt agtgagggtt aattcgc         57

<210> SEQ ID NO 28
<211> LENGTH: 57
<212> TYPE: DNA
<213> ORGANISM: Artificial Sequence
<220> FEATURE:
<223> OTHER INFORMATION: Synthetic

<400> SEQUENCE: 28
gcgtaatacg actcactata gacactgggg tactcactttt agtgagggtt aattcgc         57

<210> SEQ ID NO 29
<211> LENGTH: 51
<212> TYPE: DNA
<213> ORGANISM: Artificial Sequence
<220> FEATURE:
<223> OTHER INFORMATION: Synthetic

<400> SEQUENCE: 29
gcgaattaac cctcactaaa gtagcctcgt ctatagtgag tcgtattacg c                51

<210> SEQ ID NO 30
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: n = misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: n is a, c, g, t or u

<400> SEQUENCE: 30
gcgaattaac cctcactaaa gtacgntcgt ctatagtgag tcgtattacg c                51

<210> SEQ ID NO 31
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (25)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: n = misc_feature
<222> LOCATION: (25)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (25)..(26)
<223> OTHER INFORMATION: n is a, c, g, t or u

<400> SEQUENCE: 31
gcgaattaac cctcactaaa gtagnntcgt ctatagtgag tcgtattacg c                51

```
<210> SEQ ID NO 32
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (28)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(30)
<223> OTHER INFORMATION: n is a, c, g, t or u

<400> SEQUENCE: 32
gcgaattaac cctcactaaa gtgagtannn agtgtctata gtgagtcgta ttacgc      56

<210> SEQ ID NO 33
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (28)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: n = misc_feature
<222> LOCATION: (28)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(31)
<223> OTHER INFORMATION: n is a, c, g, t or u

<400> SEQUENCE: 33
gcgaattaac cctcactaaa gtgagtannn nagtgtctat agtgagtcgt attacgc     57

<210> SEQ ID NO 34
<211> LENGTH: 57
<212> TYPE: DNA
<213> ORGANISM: Artificial Sequence
<220> FEATURE:
<223> OTHER INFORMATION: Synthetic

<400> SEQUENCE: 34
gcgaattaac cctcactaaa gtgagtaccc cagtgtctat agtgagtcgt attacgc     57

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
gcgtaatacg actcactata g                                            21

<210> SEQ ID NO 36
<211> LENGTH: 24
<212> TYPE: DNA
<213> ORGANISM: Artificial Sequence
<220> FEATURE:
<223> OTHER INFORMATION: Synthetic
```

<400> SEQUENCE: 36
tcgcacacag gaaacagcta tgac 24

<210> SEQ ID NO 37
<211> LENGTH: 73
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (31)..(31)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: n = misc_feature
<222> LOCATION: (36)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (36)..(37)
<223> OTHER INFORMATION: n is a, c, g, t or u
<220> FEATURE:
<221> NAME/KEY: n = misc_feature
<222> LOCATION: (43)..(43)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (43)..(43)
<223> OTHER INFORMATION: n is a, c, g, t or u

<400> SEQUENCE: 37
gacactagta gcactcacta tacgtgactc ntcacnnagt gcnactacgg tcatagctgt 60
ttcctgtgtg cga 73

<210> SEQ ID NO 38
<211> LENGTH: 73
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (31)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: n = misc_feature
<222> LOCATION: (37)..(38)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (37)..(38)
<223> OTHER INFORMATION: n is a, c, g, t or u
<220> FEATURE:
<221> NAME/KEY: n = misc_feature
<222> LOCATION: (43)..(43)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (43)..(43)
<223> OTHER INFORMATION: n is a, c, g, t or u

<400> SEQUENCE: 38
tcgcacacag gaaacagcta tgaccgtagt ngcactnngt gangagtcac gtatagtgag    60
tgctactagt gtc                                                      73

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
gacactagta gcactcacta tacg                                          24

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
caggaaggag cgatcgcaac gtat                                          24

<210> SEQ ID NO 41
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (38)..(38)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (38)..(38)
<223> OTHER INFORMATION: n is a, c, g, t or u

<400> SEQUENCE: 41
ctaggacgac ggactgccta tgagagacat gagggccngg taccatcgat acgttgcgat    60
cgctccttcc tg                                                       72

<210> SEQ ID NO 42
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (35)..(35)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (35)..(35)
<223> OTHER INFORMATION: n is a, c, g, t or u

<400> SEQUENCE: 42
caggaaggag cgatcgcaac gtatcgatgg taccnggccc tcatgtctct cataggcagt    60
ccgtcgtcct ag                                                       72

<210> SEQ ID NO 43
<211> LENGTH: 72
<212> TYPE: DNA
<213> ORGANISM: Artificial Sequence
<220> FEATURE:
<223> OTHER INFORMATION: Synthetic

<400> SEQUENCE: 43
ctaggacgac ggactgccta tgagagacat gagggcccgg taccatcgat acgttgcgat    60
cgctccttcc tg                                                        72

<210> SEQ ID NO 44
<211> LENGTH: 72
<212> TYPE: DNA
<213> ORGANISM: Artificial Sequence
<220> FEATURE:
<223> OTHER INFORMATION: Synthetic

<400> SEQUENCE: 44
caggaaggag cgatcgcaac gtatcgatgg taccgggccc tcatgtctct cataggcagt    60
ccgtcgtcct ag                                                        72

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
ctaggacgac ggactgccta tgag                                           24

<210> SEQ ID NO 46
<211> LENGTH: 97
<212> TYPE: DNA
<213> ORGANISM: Artificial Sequence
<220> FEATURE:
<223> OTHER INFORMATION: Synthetic

<400> SEQUENCE: 46
ggcgtaatac gactcactat aggctctgta gttcagtcgg tagaacggcg gacttccaat    60
ccgtatgtca ctggttcgag tccagtcaga gccgcca                             97

<210> SEQ ID NO 47
<211> LENGTH: 97
<212> TYPE: DNA
<213> ORGANISM: Artificial Sequence
<220> FEATURE:
<223> OTHER INFORMATION: Synthetic

<400> SEQUENCE: 47
tggcggctct gactggactc gaaccagtga catacggatt ggaagtccgc cgttctaccg    60
actgaactac agagcctata gtgagtcgta ttacgcc                             97

<210> SEQ ID NO 48
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (55)..(55)
<223> OTHER INFORMATION: 2-amino-8-(1'-beta-D-2'-deoxyribofuranosyl)-
      imidazo[1,2-a]-1,3,5-triazin-4(8H)-one

```
<220> FEATURE:
<221> NAME/KEY: misc_feature
<222> LOCATION: (55)..(55)
<223> OTHER INFORMATION: n is a, c, g, t or u

<400> SEQUENCE: 48
ggcgtaatac gactcactat aggctctgta gttcagtcgg tagaacggcg gactnccaat    60
ccgtatgtca ctggttcgag tccagtcaga gccgcca                            97

<210> SEQ ID NO 49
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (43)..(43)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (43)..(43)
<223> OTHER INFORMATION: n is a, c, g, t or u

<400> SEQUENCE: 49
tggcggctct gactggactc gaaccagtga catacggatt ggnagtccgc cgttctaccg    60
actgaactac agagcctata gtgagtcgta ttacgcc                            97

<210> SEQ ID NO 50
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (56)..(56)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (56)..(56)
<223> OTHER INFORMATION: n is a, c, g, t or u

<400> SEQUENCE: 50
ggcgtaatac gactcactat aggctctgta gttcagtcgg tagaacggcg gacttncaat    60
ccgtatgtca ctggttcgag tccagtcaga gccgcca                            97

<210> SEQ ID NO 51
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (42)..(42)
<223> OTHER INFORMATION: 6-amino-3-(2'-deoxy)-D-ribofuranosyl)-5-nitro-
      1H-pyridin-2-one
<220> FEATURE:
<221> NAME/KEY: n = misc_feature
<222> LOCATION: (42)..(42)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (42)..(42)
<223> OTHER INFORMATION: n is a, c, g, t or u
```

<400> SEQUENCE: 51
tggcggctct gactggactc gaaccagtga catacggatt gnaagtccgc cgttctaccg    60
actgaactac agagcctata gtgagtcgta ttacgcc    97

<210> SEQ ID NO 52
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (57)..(57)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (57)..(57)
<223> OTHER INFORMATION: n is a, c, g, t or u

<400> SEQUENCE: 52
ggcgtaatac gactcactat aggctctgta gttcagtcgg tagaacggcg gacttcnaat    60
ccgtatgtca ctggttcgag tccagtcaga gccgcca    97

<210> SEQ ID NO 53
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (41)..(41)
<223> OTHER INFORMATION: 6-amino-3-(2'-deoxy)-D-ribofuranosyl)-5-nitro-
      1H-pyridin-2-one
<220> FEATURE:
<221> NAME/KEY: n = misc_feature
<222> LOCATION: (41)..(41)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
<223> OTHER INFORMATION: n is a, c, g, t or u

<400> SEQUENCE: 53
tggcggctct gactggactc gaaccagtga catacggatt ngaagtccgc cgttctaccg    60
actgaactac agagcctata gtgagtcgta ttacgcc    97

<210> SEQ ID NO 54
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (55)..(55)
<223> OTHER INFORMATION: 6-amino-3-(2'-deoxy)-D-ribofuranosyl)-5-nitro-
      1H-pyridin-2-one
<220> FEATURE:
<221> NAME/KEY: n = misc_feature
<222> LOCATION: (55)..(55)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (55)..(55)
<223> OTHER INFORMATION: n is a, c, g, t or u

```
<400> SEQUENCE: 54
ggcgtaatac gactcactat aggctctgta gttcagtcgg tagaacggcg gactnccaat      60
ccgtatgtca ctggttcgag tccagtcaga gccgcca                              97

<210> SEQ ID NO 55
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (43)..(43)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (43)..(43)
<223> OTHER INFORMATION: n is a, c, g, t or u

<400> SEQUENCE: 55
tggcggctct gactggactc gaaccagtga catacggatt ggnagtccgc cgttctaccg      60
actgaactac agagcctata gtgagtcgta ttacgcc                              97

<210> SEQ ID NO 56
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (56)..(56)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (56)..(56)
<223> OTHER INFORMATION: n is a, c, g, t or u

<400> SEQUENCE: 56
ggcgtaatac gactcactat aggctctgta gttcagtcgg tagaacggcg gacttncaat      60
ccgtatgtca ctggttcgag tccagtcaga gccgcca                              97

<210> SEQ ID NO 57
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (42)..(42)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (42)..(42)
<223> OTHER INFORMATION: n is a, c, g, t or u

<400> SEQUENCE: 57
tggcggctct gactggactc gaaccagtga catacggatt gnaagtccgc cgttctaccg      60
actgaactac agagcctata gtgagtcgta ttacgcc                              97
```

-continued

<210> SEQ ID NO 58
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (57)..(57)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (57)..(57)
<223> OTHER INFORMATION: n is a, c, g, t or u

<400> SEQUENCE: 58
ggcgtaatac gactcactat aggctctgta gttcagtcgg tagaacggcg gacttcnaat    60
ccgtatgtca ctggttcgag tccagtcaga gccgcca                            97

<210> SEQ ID NO 59
<211> LENGTH: 97
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (41)..(41)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (41)..(41)
<223> OTHER INFORMATION: n is a, c, g, t or u

<400> SEQUENCE: 59
tggcggctct gactggactc gaaccagtga catacggatt ngaagtccgc cgttctaccg    60
actgaactac agagcctata gtgagtcgta ttacgcc                            97

<210> SEQ ID NO 60
<211> LENGTH: 76
<212> TYPE: DNA
<213> ORGANISM: Artificial Sequence
<220> FEATURE:
<223> OTHER INFORMATION: Synthetic

<400> SEQUENCE: 60
ggcucuguag uucagucggu agaacggcgg acuuccaauc cguaugucac ugguucgagu    60
ccagucagag ccgcca                                                   76

<210> SEQ ID NO 61
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (34)..(34)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (34)..(34)
<223> OTHER INFORMATION: n is a, c, g, t or u

<400> SEQUENCE: 61
ggcucuguag uucagucggu agaacggcgg acunccaauc cguaugucac ugguucgagu    60
ccagucagag ccgcca                                                   76

<210> SEQ ID NO 62
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (35)..(35)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (35)..(35)
<223> OTHER INFORMATION: n is a, c, g, t or u

<400> SEQUENCE: 62
ggcucuguag uucagucggu agaacggcgg acuuncaauc cguaugucac ugguucgagu    60
ccagucagag ccgcca                                                   76

<210> SEQ ID NO 63
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (36)..(36)
<223> OTHER INFORMATION: 2-amino-8-(1'-beta-D-2'-deoxyribofuranosyl)-
      imidazo[1,2-a]-1,3,5-triazin-4(8H)-one
<220> FEATURE:
<221> NAME/KEY: misc_feature
<222> LOCATION: (36)..(36)
<223> OTHER INFORMATION: n is a, c, g, t or u

<400> SEQUENCE: 63
ggcucuguag uucagucggu agaacggcgg acuucnaauc cguaugucac ugguucgagu    60
ccagucagag ccgcca                                                   76

<210> SEQ ID NO 64
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: n is a, c, g, t or u

<400> SEQUENCE: 64
ggcucuguag uucagucggu agaacggcgg acunccaauc cguaugucac ugguucgagu    60
ccagucagag ccgcca                                                   76

```
<210> SEQ ID NO 65
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (35)..(35)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (35)..(35)
<223> OTHER INFORMATION: n is a, c, g, t or u

<400> SEQUENCE: 65
ggcucuguag uucagucggu agaacggcgg acuuncaauc cguaugucac ugguucgagu      60
ccagucagag ccgcca                                                      76

<210> SEQ ID NO 66
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: n = misc_feature
<222> LOCATION: (36)..(36)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (36)..(36)
<223> OTHER INFORMATION: n is a, c, g, t or u

<400> SEQUENCE: 66
ggcucuguag uucagucggu agaacggcgg acuucnaauc cguaugucac ugguucgagu      60
ccagucagag ccgcca                                                      76
```

AMPLIFICATION OF OLIGONUCLEOTIDES CONTAINING NON-STANDARD NUCLEOTIDES BY POLYMERASE CHAIN REACTIONS

CROSS REFERENCE TO RELATED APPLICATIONS

This application is a continuation-in-part of U.S. patent application Ser. No. 14/082,800 (currently pending, filed 19 Nov. 2013), which was a continuation-in-part of U.S. patent application Ser. No. 13/493,172 (filed 11 Jun. 2012, now issued as U.S. Pat. No. 8,586,303), which was a continuation-in-part of U.S. patent application Ser. No. 12/999,138 (filed 15 Dec. 2012, now issued as U.S. Pat. No. 8,614,072), which was the United States national stage application of International Patent Application No. PCT/US2009/003595 (filed 16 Jun. 2009), which claims the benefit of U.S. Provisional Patent Application No. 61/132,225 (filed 17 Jun. 2008). This application is also a continuation-in-part of co-pending U.S. patent application Ser. No. 14/138,532 (filed 15 Jan. 2014), which was a continuation-in-part of U.S. patent Application Ser. No. 12/999,138. The disclosures of all of these applications are hereby incorporated by reference in their entirety, including all figures, tables and sequences.

STATEMENT OF RIGHTS TO INVENTIONS MADE UNDER FEDERALLY-SPONSORED RESEARCH

This invention was made with government support under Defense Threat Reduction Agency grant HDTRA1-08-0052. The government has certain rights in the invention.

THE NAMES OF PARTIES TO A JOINT RESEARCH AGREEMENT

Not applicable

INCORPORATION BY REFERENCE OF MATERIAL SUBMITTED ON A COMPACT DISK

None

BACKGROUND OF THE INVENTION

1. Field of the Invention

This invention relates to nucleotide analogs and their derivatives (termed non-standard nucleotides) that, when incorporated into DNA and RNA, expand the number of replicatable nucleotides beyond the four found in standard DNA and RNA. The invention further relates to processes that incorporate those non-standard nucleotide analogs into oligonucleotide products using the corresponding triphosphate derivatives, and more specifically, polymerases and non-standard nucleoside triphosphates that support the polymerase chain reaction (PCR) reaction with these, including PCR where the products contain more than one non-standard nucleotide.

2. Description of the Related Art

Natural oligonucleotides bind to complementary oligonucleotides according to the well-known rules of nucleobase pairing first elaborated by Watson and Crick in 1953, where adenine (A) pairs with thymine (T) (or uracil, U, in RNA), and guanine (G) pairs with cytosine (C), with the complementary strands anti-parallel to each other. These rules arise from two principles of complementarity, size-complementarity (large purines pair with small pyrimidines) and hydrogen bonding complementarity (hydrogen bond donors pair with hydrogen bond acceptors).

It is now well established in the art that the number of independently replicable nucleotides in DNA can be increased, where the size- and hydrogen binding complementarities are retained, but where different heterocycles (nucleobase analogs) attached to the sugar-phosphate backbone implement different hydrogen bonding patterns. As many as eight different nucleobase analogs forming four additional nucleobase pairs are conceivable (see, for example, [Benner, S. A. (1995) Non-standard Base Pairs with Novel Hydrogen Bonding Patterns. U.S. Pat. No. 5,432,272 (Jul. 11, 1995)]). This has led to an "artificially expanded genetic information system" (AEGIS). The ability of pairing between the additional nucleobase pairs to support DNA duplex stability has had substantial use in diagnostics. In this disclosure, DNA includes oligonucleotides containing AEGIS nucleic acids and their analogs in linear and non-linear topologies, including as dendrimers, comb-structures, and nanostructures, and these oligonucleotides and their analogs carrying tags (e.g., fluorescent, functionalized, or binding) to the ends, sugars, or nucleobases.

It would be useful to amplify oligonucleotides containing AEGIS components in processes analogous to the well-known polymerase chain reaction (PCR), here defined as a process involving thermal cycling, where the heat step denatures a duplex formed at each cycle to allow a new set of primers to bind. If PCR could be implemented with expanded DNA AEGIS alphabets, it would have many uses, including (without limitation) DNA and RNA-targeted diagnostics, and in vitro selection and evolution to create catalysts, ligands, and receptors.

Various items in the art describe efforts to use the U.S. Pat. No. 5,432,272 nucleobases with polymerases to support PCR. However, these generally failed to sustain PCR over more than five heat-cool cycles, since polymerases that incorporate non-standard base pairs into duplexes with sufficient efficiency and fidelity to support PCR were not described. This failure is illustrated by Johnson et al. [Johnson, S. C., Sherrill, C. B., Marshall, D. J., Moser, M. J., Prudent, J. R. (2004) A third base pair for the polymerase chain reaction: inserting isoC and isoG. *Nucl. Acids Res.* 32, 1937-1941], who attempted to incorporate the isocytosine and isoguanine disclosed in U.S. Pat. No. 5,432,272 into PCR. As their publication shows, the non-standard component is not retained in the product, to an extent greater than 90% over 5 cycles. Indeed, their FIG. 2 showed that only ~90% of the isoC:isoG pair remained after just one cycle, and only ~80% was retained after seven cycles. This can be used as a metric for the utility of a PCR process that incorporates a non-standard nucleobase pair. In this case, the loss was attributed to the ability of a minor tautomeric form of isoguanosine to pair with thymidine, as well as contacts that thermostable polymerases (the kind that are needed for useful PCR, as they survive heating to at least 80° C. for the purpose of separating strands) make to unshared electrons in the minor groove, which are delivered by DNA from the exocyclic C=O groups of C and T, and N3 of A and G.

Many enzymes work well with AEGIS components, including kinases, ligases, and even ribosomes [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539]. Polymerases, in contrast, accept many non-standard components of DNA only inefficiently, judging by rate, processivity, fidelity, or some combination of these [Horlacher, J., Hottiger, M., Podust, V. N., Hübscher, U. and Benner, S. A. (1995) Expanding the genetic alphabet: Recognition by viral and cellular DNA polymerases of nucleosides bearing bases with non-standard hydrogen bonding patterns, *Proc. Natl. Acad. Sci.* 92, 6329-6333]. These inefficiencies need not prevent the utility of polymerase-based incorporation of AEGIS components in single pass experiments, and may not be apparent with standing start experiments, where the non-standard triphosphate is the first nucleotide to be added to a primer, or a running start experiment, where the polymerase adds standard nucleotides before it is challenged to incorporate a non-standard nucleotide. However, they defeat sustained amplification by PCR where over 90% of the nucleobase is retained after the first theoretical cycle, here defined as "useful PCR".

Thus, U.S. Pat. No. 5,432,272 nor the prior art do not enable useful PCR of DNA containing non-standard nucleotides (AEGIS components). While it is recognized by those of ordinary skill in the art, and taught here, that PCR processes invariably introduce some mutations, and that some daughter oligonucleotides will not have the exact identical sequence as the original oligonucleotide (and indeed, sequence evolution due to this infidelity is useful for doing in vitro evolution, see U.S. Pat. No. 8,586,303), PCR amplification of these oligonucleotides would be most useful if the level of mutation is lower rather than higher, preferably less than a 5% loss of the non-standard nucleobase per cycle, and more preferably less than a 2% loss of the non-standard nucleobase per cycle, and in any case retaining 90% of the AEGIS component after the first cycle.

U.S. Pat. No. 8,354,225 (Ser. No. 11/371,497) attempted to achieve a less ambitious process, here with an extra nucleotide pair formed between diaminopyrimidine and either xanthosine or 5-azo-7-deazaxanthosine, one that did not involve thermocycling. This was shown to be possible with a mutant form of the reverse transcriptase from HIV. Unfortunately, reverse transcriptases are not thermally stable upon heating to 80° C. (or, in most cases, even above 50° C.), and therefore cannot support PCR. Indeed, U.S. Pat. No. 8,354,225 required an addition of more reverse transcriptase after each heat step. Further, the other pyrimidine nucleoside analogs that U.S. Pat. No. 8,354,225 disclosed had nucleobases based on a pyrazine ring system, now known to epimerize rapidly. Finally, the structure disclosed by U.S. Pat. No. 8,354,225 to implement the purine analog with a hydrogen bond donor-donor-acceptor pattern is now known to be nonfunctional, and the pyrimidine analog shown to implement the hydrogen bond donor-donor-acceptor pattern lacks a methyl group and is now known to be unstable with respect to depyrimidinylation. FIG. 1 summarizes these deficiencies.

For these reasons, despite the widespread recognition of the value of PCR using non-standard nucleobases, if it could be achieved, many in the art considered this goal unachievable.

BRIEF SUMMARY OF THE INVENTION

This invention covers processes for the PCR amplification of oligonucleotides that incorporate designated components of an artificially expanded genetic information system (FIG. 2), as well as the compositions of matter that those amplifications produce, as well as polymerases that accept them.

BRIEF DESCRIPTION OF THE DRAWINGS

Drawing 1.

Drawing 2.

Drawing 3.

Drawing 4.

Drawing 5.

Drawing 6.

Drawing 7.

Drawing 8.

Drawing 9.

Drawing 10.

Drawing 11.

Drawing 12.

Drawing 13.

Drawing 14.

Drawing 15.

Drawing 16.

Drawing 17.

Drawing 18.

Drawing 19.

DESCRIPTION OF THE INVENTION

Figure 1:
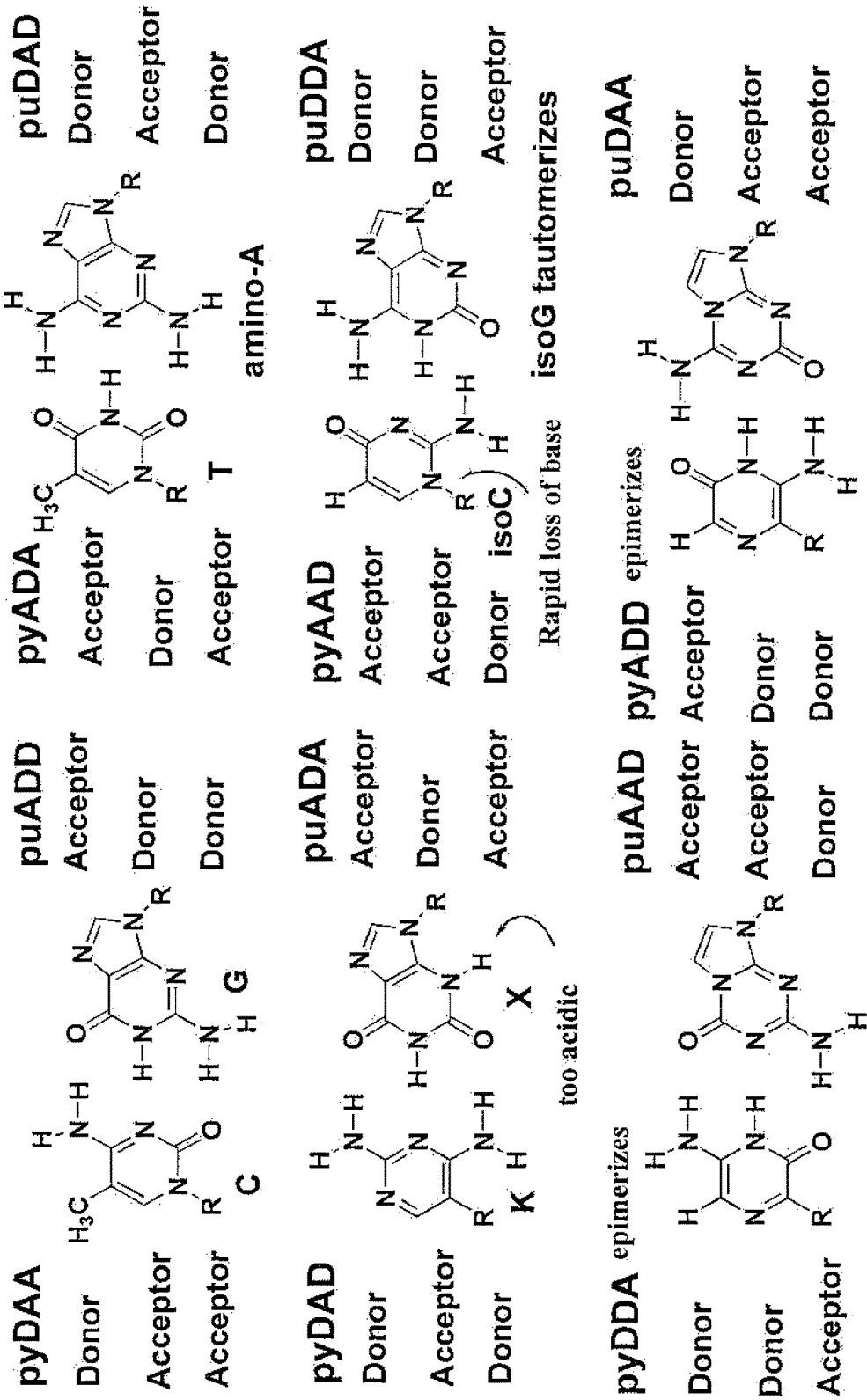
FIG. 1. Implementations of AEGIS nucleobases disclosed by U.S. Pat. No. 8,354,225. The nucleobase implementing the puDDA pattern suffers from large tautomeric ambiguity. The implementations on pyrazine rings suffer from facile epimerization. The implementation on a simple pyridine is too basic and prone to oxidation.

A central teaching of this disclosure is that hydrogen-bonding pattern designated using this systematic nomenclature is distinct, in concept, from the organic molecule that is used to implement the hydrogen-bonding pattern. Which organic molecule is chosen to implement a specific hydrogen-bonding pattern determines, in large part, the utility of the non-standard hydrogen-bonding pattern, in various applications to which it might be applied.

Thus, guanosine is a nucleoside that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups.

Likewise, isoguanosine is a nucleoside that implements the puDDA hydrogen-bonding pattern. So does, however, 7-deazaisoguanosine, 3-deazaisoguanosine, 3,7-dideazaisoguanosine, and any of any number of other purines and purine derivatives, including those that carry side chains to which are appended functional groups, such as fluorescent, fluorescent quencher, attachment, or metal complexing groups, on the exocyclic amino group or at position 7.

Likewise, xanthine is a nucleobase that implements the puADA hydrogen-bonding pattern. So does, however, imidazo[1,2-a]-1,3,5-triazine-2(8H)-4(3H)-dione, and any of any number of other purines and purine derivatives, including those that carry side chains to which are appended functional groups, such as fluorescent, fluorescent quencher, attachment, or metal complexing groups.

The presently preferred embodiments of the instant invention with respect to eight non-standard nucleotides, which form four base pairs, is now presented, with reference (and/or cross-reference) to systematic nomenclature. Numbering is based on the deoxyribonucleoside analog.

For the pyDAD hydrogen bonding pattern ("py" indicates that the heterocycle is a pyrimidine analog; contrast with "pu", which indicates a purine analog), the presently preferred embodiment is 2,4-diamino-5-(1'-beta-D-2'-deoxyribofuranosyl)-pyrimidine, also named (1R)-1,4-anhydro-2-deoxy-1-C-(2,4-diamino-5-pyrimidinyl)-D-erythropentitol, or the 2,6-diamino-3-nitro-5-(1'-beta-D-2'-deoxyribofuranosyl)-pyridine.

For the puADA hydrogen bonding pattern, the presently preferred embodiment is 8-(β-D-2'-deoxyribofuranosyl)imidazo[1,2-a]-1,3,5-triazine-2(8H)-4(3H)-dione, including those that carry side chains attached to "C7", including those to which are appended functional groups, such as fluorescent, fluorescent quencher, attachment, or metal complexing groups.

For the pyAAD hydrogen bonding pattern, the presently preferred embodiment is 2'-deoxy-5-methylisocytidine (2-amino-5-methyl-1-(1'-beta-D-2'-deoxyribofuranosyl)-4 (1H)-pyrimidinone) or 2-deoxy-N-methyl-pseudocytidine.

For the puDDA hydrogen bonding pattern, the presently preferred embodiment is 6-amino-1,9-dihydro-9-(1'-beta-D-2'-deoxyribofuranosyl)-3H-7-deazapurin-2-one, including those that carry side chains attached to the exocyclic amino group or to "C7", including those to which are appended functional groups, such as fluorescent, fluorescent quencher, attachment, or metal complexing groups.

For the pyDDA hydrogen bonding pattern, the presently preferred embodiment is 6-amino-3-(2'-deoxy)-D-ribofuranosyl)-5-nitro-1H-pyridin-2-one.

For the puAAD hydrogen bonding pattern, the presently preferred embodiment is 7-amino-9-(1'-beta-D-2'-deoxyribofuranosyl)-imidazo[1,2-c]-pyrimidin-5(1H)-one, including those that carry side chains attached to "C7", including those to which are appended functional groups, such as fluorescent, fluorescent quencher, attachment, or metal complexing groups.

For the pyADD hydrogen bonding pattern, the presently preferred embodiment is 2-amino-3-(2'-deoxy)-D-ribofuranosyl)-5-nitro-1H-pyridin-6-one.

For the puDAA hydrogen bonding pattern, the presently preferred embodiment is 4-amino-8-(1'-beta-D-2'-deoxyribofuranosyl)-imidazo[1,2-a]-1,3,5-triazin-2(8H)-one, including those that carry side chains attached to the exocyclic amino group or to "C7", including those to which are appended functional groups, such as fluorescent, fluorescent quencher, attachment, or metal complexing groups.

To practice the invention, standard PCR is performed to increase the number of copies (to "amplify") of a starting oligonucleotide. PCR is performed with a thermostable polymerase, which is defined as a polymerase that is stable at temperatures up to at least 80° C., and at temperatures that allow duplex DNA to be separated. Several of the preferred polymerases, matched to preferred AEGIS components, are described in the Examples, which include standard thermostable polymerases from evolutionary Family A (e.g. Taq DNA polymerase from Family A) and from Family B (e.g. Deep Vent polymerase). These include mutant forms of various thermostable polymerases, some disclosed in the Examples, which also represent inventions.

The PCR requires dissolving the oligonucleotide to be amplified in an aqueous mixture containing a thermostable DNA polymerase in a buffer where the polymerase functions, as is known in the art. The aqueous mixture must also contain nucleoside triphosphates that are Watson-Crick complementary to all of the nucleotides in the oligonucleotide to be amplified. "Watson Crick complementary" is a term of art that requires the heterocycles in the triphosphate to be size- and hydrogen bonding-complementary, as outlined above.

The PCR mixture also must contain a first oligonucleotide primer that is "substantially complementary" to a segment at or near the 3'-end of the oligonucleotide to be amplified. "Substantially complementary" is a term of art that includes the possibility that the primer:oligonucleotide complex has a small number of mismatches; the level of mismatching must not, however, be so large as to prevent the hybridization of the primer to the oligonucleotide to be amplified. This hybridization is achieved by annealing of the primer and the oligonucleotide by lowering the temperature of the mixture, typically starting at a temperature above 80° C. where duplexes are unstable, at an appropriate rate, as is well known in the art, to a temperature where the hybrid is substantially stable.

The first extension in the PCR arises by incubating the mixture of primer, oligonucleotide, polymerase, and triphosphates at a temperature where the polymerase extends the first oligonucleotide primer to give an extension product that is substantially complementary to the oligonucleotide. In the initial product, the extension product forms a duplex with said oligonucleotide. Further, the extension product, when it is separated from said oligonucleotide, can hybridize to a second oligonucleotide primer, which that a sequence substantially identical to a portion of said oligonucleotide at or near its 5'-end, and is therefore substantially complementary to the extension product at its 3'-end. This primer extension time is variable, as is known in the art, but preferably is between 30 seconds and three minutes.

For the process to continue, the temperature of the mixture is then increased to a temperature sufficient to separate the initial oligonucleotide from its extension product. This gives both primers a chance to bind upon subsequent annealing, the first primer to the original oligonucleotide, the second to the extension product. This temperature is generally above 80° C. The annealing is then achieved by lowering the temperature of the mixture to a temperature at which the primers can hybridize. Typically, the temperature is then adjusted to a temperature optimal for the polymerase to extend all primer-template complexes.

These steps are repeated an arbitrary number of times, but generally at least five times. The extent of amplification depends on the ratio of primers to original oligonucleotide. As is known in the art, unequal amounts of the two primers give "asymmetric PCR".

EXAMPLES

Example 1

PCR Amplification of the Diaminopurine (K):5-aza-7-deazaxanthine (X) Pair

Variants of the DNA polymerase 1 from *Thermus aquaticus* that incorporate the K:X nucleobase pair were obtained by screening a large library of variants constructed by analyzing heterotachy within the protein family. After screening, 23 of the most active clones were selected to do a PCR with a reduced optimal extension time (reduced from 2:10 to 1:10) that incorporated the nucleobase pair between diaminopyrimidine (here, abbreviated as K) and 5-aza-7-deazaxanthosine (here, abbreviated as X). Plasmids encoding the variants were then prepped from cultures expressing the polymerase variants having higher activity (judged from the amount of PCR product). Five of these polymerases were partially sequenced to identify their mutations.

Figure 3:
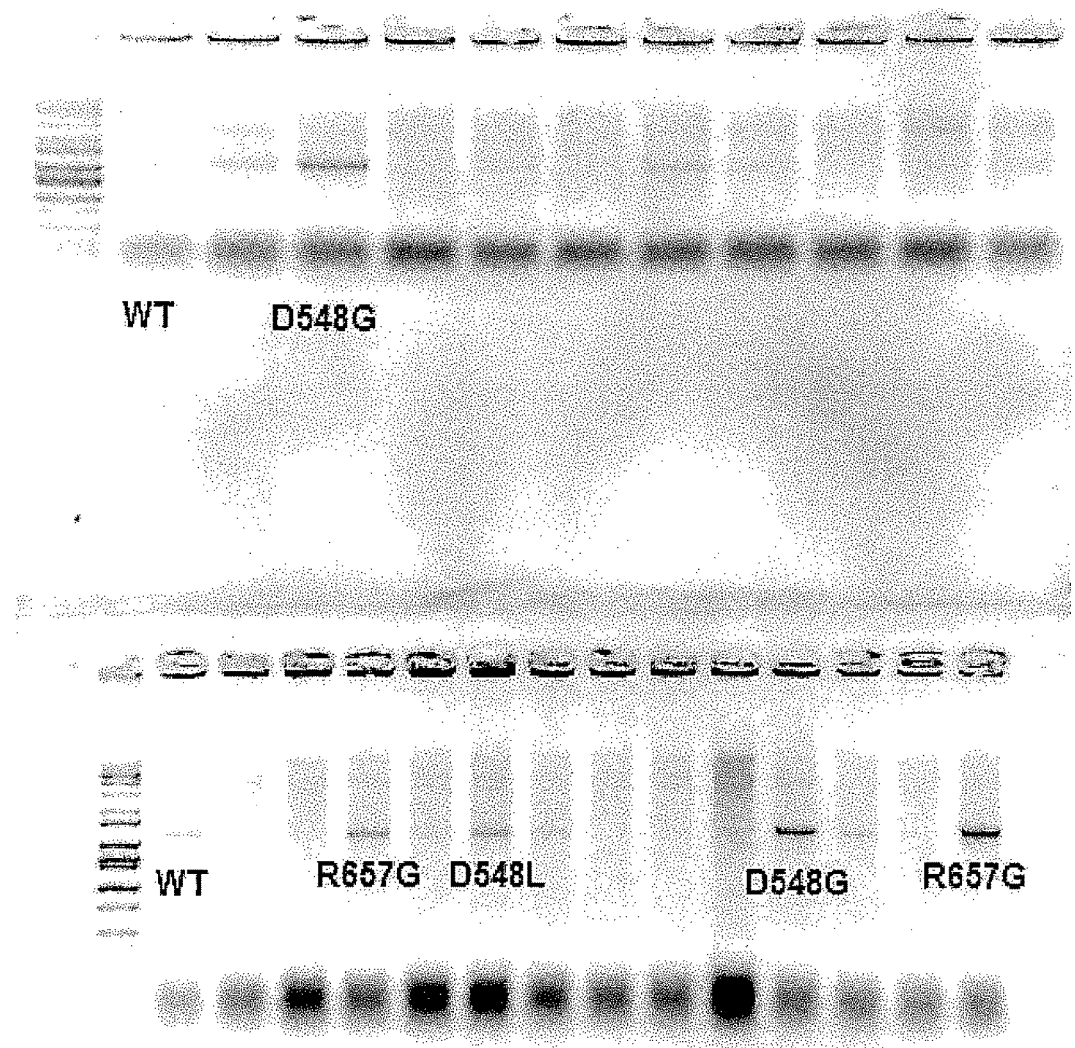
FIG. 3. PCR products incorporating K:X pairs (Example 1) showing variants of the DNA polymerase 1 from *Thermus aquaticus* that PCR amplify products by incorporating dKTP opposite template X and dXTP opposite template K. The polymerases have replaced aspartic acid at position 548 by glycine, arginine at position 657 by glycine, aspartic acid at position 548 by leucine, aspartic acid at position 548 by a glycine, and arginine at position 657 by glycine.

FIG. 3 shows data identifying polymerases that perform in the instant process. The polymerases replace the aspartic acid at position 548 by a glycine, the arginine at position 657 by a glycine, the aspartic acid at position 548 by a leucine, the aspartic acid at position 548 by a glycine, and the arginine at position 657 by a glycine. This numbering differs by −3 amino acids from standard numbering. Thus, the 657 site hold the arginine at site 660 (in standard numbering) in the O-helix. This helix also contains Arg 659 and Lys 663, which are known to interact with the incoming triphosphate moiety and are critical for enzymatic activity.

TABLE 1

Taq variants found after screening.

| Variant | Standard numbering | Distance to aspartate 785 (Å) |
|---|---|---|
| D548G | 551 | 293 |
| D548L | 551 | 29.5 |
| R657G | 660 | 14.1 |

The primers were designed so that successful amplification required both dKTP to be incorporated opposite template X and dXTP to be incorporated opposite template K.

Fwd-K-17
SEQ ID NO 1
5'-CTAKGACKACGKACTKC-3'

Rev-X-17
SEQ ID NO 2
5'C-AGXAAGXAGCXATCXC-3'

Fwd K-59
SEQ ID NO 3
5'-CTAKGACKACGKACTKCCACCAGGAAGCAGCCATCACACACAGTGCGC
ATCCTGACTGC-3'

Rev X-60
SEQ ID NO 4
5'CAGXAAGXAGCXATCXCCACCAGGAAGCAGCCATCACACACCCAAGGGG
TTATGCTAGGG-3'

To perform the PCR, 25 million cells expressing the Taq polymerase variant were suspended in 30 µL of master mix and placed on the thermocycler on the following program: 94° C. for 2:0 min, then 30 cycles at [94° C. for 30 sec 57° C. for 30 sec 72° C. for 1.17 min], finally 72° C. for 10:00 min, in a thermocycler. The PCR used this master mix:

| component | concentration | Volume (µL) |
| --- | --- | --- |
| 10X Thermo pol pH 8.8 | 10X | 80 |
| Fwd K59 | 0.2 uM | 80 |
| Rev X60 | 0.2 uM | 80 |
| Fwd K17 | 2 uM | 80 |
| Rev X17 | 2 uM | 80 |
| dNTPs | 2 mM | 80 |
| dXTP | 2 mM | 16 |
| dKTP | 2 mM | 16 |
| water | | 288 |

Example 2

PCR Amplification of the 5-methylisocytosine Analogs and Isoguanine Analogs

Johnson et al. [2004] lost isocytosine and isoguanosine in the art PCR. Accordingly, new nucleobases carrying heterocycles that implement the same hydrogen bonding patterns, but not suffering from the defects of the species known in the art, were examined. Instead of 2'-deoxyisocytidine, the PCR amplifications of the instant invention used 2'-deoxy-5-methylisocytidine and 2'-deoxy-5-methylpseudocytidine [Kim, H. J., Leal, N. A., Benner, S. A. (2009) 2'-Deoxy-1-methylpseudocytidine. A stable analog of 2'-deoxy-5-methylisocytidine. *Bioorg. Med Chem.* 17, 3728-3732]. Instead of 2'-deoxy-isoguanosine, the PCR amplifications of the instant invention used 2'-deoxy-7-deazaisoguanosine and a cyclic version of 2'-deoxy-7-deazaisoG. Here, fidelity studies used a $^{32}$P-radiolabeled primer to monitor the incorporation of AEGIS triphosphates opposite isoC and psuedoC in a template. In these experiments, the template contains a BglII restriction site which cuts at 5'-A↓GATCT. That site is disrupted by a nucleotide analog that implements the pyAAD and/or puDDA hydrogen bonding pattern. Replacement of the AEGIS pair by an A:T pair restores the restriction site. Analysis of the PCR products therefore allows the measurement of the fidelity of the PCR. Also, a control template containing the BglII site with standard dNTPs was tested in PCRs. This analysis assumes:
1. A restriction enzyme that recognizes the T:A pair will not recognize a pair between an analog of isoC:isoG.
2. Loss of an isoC:isoG analog pair gives only T:A, and never C:G, G:C, or A:T.

To approximate various cycles, various dilutions of template were used with the following modifications:
  1) Amplify using primers and dNTPs
  2) Amplify using primers, dNTPs, disoCTP and disoGTP
  3) Amplify using primers, dNTPs, pseudoCTP and d7deazaisoGTP
  4) Amplify using primers, dNTPs, pseudoCTP and cyclic d7deazaisoGTP As shown in the figures, PCRs generated full length products as 60 mers. After dilution of the template in 10-fold increments starting at $10^{10}$ molecules to $10^7$ molecules and 30 rounds of PCR, PCR products were digested with BglII. Also, products containing 5'-methylisoC were treated with acid to cleave the oligonucleotide at the site containing the isoC analog, neutralized and resolved on 16% PAGE. As the pair is replaced by T:A, the amount of acid hydrolyzed product decreases, while the amount of BglII digested product increases.

Olignucleotides Used:

tauto T BgIIIXhoI (60 nt)
SEQ ID NO 5
5'-GCG TAA TAC GAC TCA CTA TAG ACG AGC TAG ATC TCG
AGT CTT TAG TGA GGG TTA ATT CGC tauto iC BgIIIXhoI
SEQ ID NO 6
5'-GCG TAA TAC GAC TCA CTA TAG ACG AGC
TAG ATC MeisoCCG AGT CTT TAG TGA GGG TTA ATT CGC tauto S BelIIXhoI
SEQ ID NO 7
5'-GCG TAA TAC GAC TCA CTA TAG ACG AGC
TAG ATC pseudoCCG AGT CTT TAG TGA GGG TTA ATT CGC Forward primer (21 nt) nal P-2f
SEQ ID NO 8
32P-5'-GCG TAA TAC GAC TCA CTA TAG Reverse primer (21 nt) nal P-2r
SEQ ID NO 9
5'-GCG AAT AAC CCT CTA CTA AAG

TABLE 1

Amounts of full length product, BglII digested and acid hydrolyzed product from PCRs seen in FIG. 1 were quantified

| | Template molecules | [1]Theoretical rounds (n) | | [3]Volume (CNT * mm²) | % digested or cleaved |
| --- | --- | --- | --- | --- | --- |
| Template T dNTPs | $6 \times 10^{10}$ | 3.32 | [2]FLP | 13206 | 90 |
| | | | BglII digested | 117735 | |
| | $6 \times 10^9$ | 6.64 | FLP | 4580 | 96 |
| | | | BglII digested | 122357 | |

TABLE 1-continued

Amounts of full length product, BglII digested and acid hydrolyzed
product from PCRs seen in FIG. 1 were quantified

| | Template molecules | [1]Theoretical rounds (n) | | [3]Volume (CNT * mm$^2$) | % digested or cleaved |
|---|---|---|---|---|---|
| | $6 \times 10^8$ | 9.97 | FLP | 12716 | 90 |
| | | | BglII digested | 111817 | |
| | $6 \times 10^7$ | 13.29 | FLP | 1292 | 98 |
| | | | BglII digested | 69162 | |
| Template isoC isoC/isoG | $6 \times 10^{10}$ | 3.32 | FLP | 17973 | 83 RE |
| | | | BglII digested | 85099 | |
| | | | FLP | 46965 | 22 |
| | | | cleaved | 12968 | |
| | $6 \times 10^9$ | 6.64 | FLP | 29232 | 77 |
| | | | BglII digested | 99881 | |
| | | | FLP | 63661 | 10 |
| | | | cleaved | 7016 | |
| | $6 \times 10^8$ | 9.97 | FLP | 16857 | 85 |
| | | | BglII digested | 99100 | |
| | | | FLP | 62763 | 4 |
| | | | cleaved | 2730 | |
| | $6 \times 10^7$ | 13.29 | FLP | 2343 | 96 |
| | | | BglII digested | 54607 | |
| | | | FLP | 24942 | 4 |
| | | | cleaved | 907 | |

PCR, Acid Hydrolysis and Restriction Digestion Conditions

Figure 4:
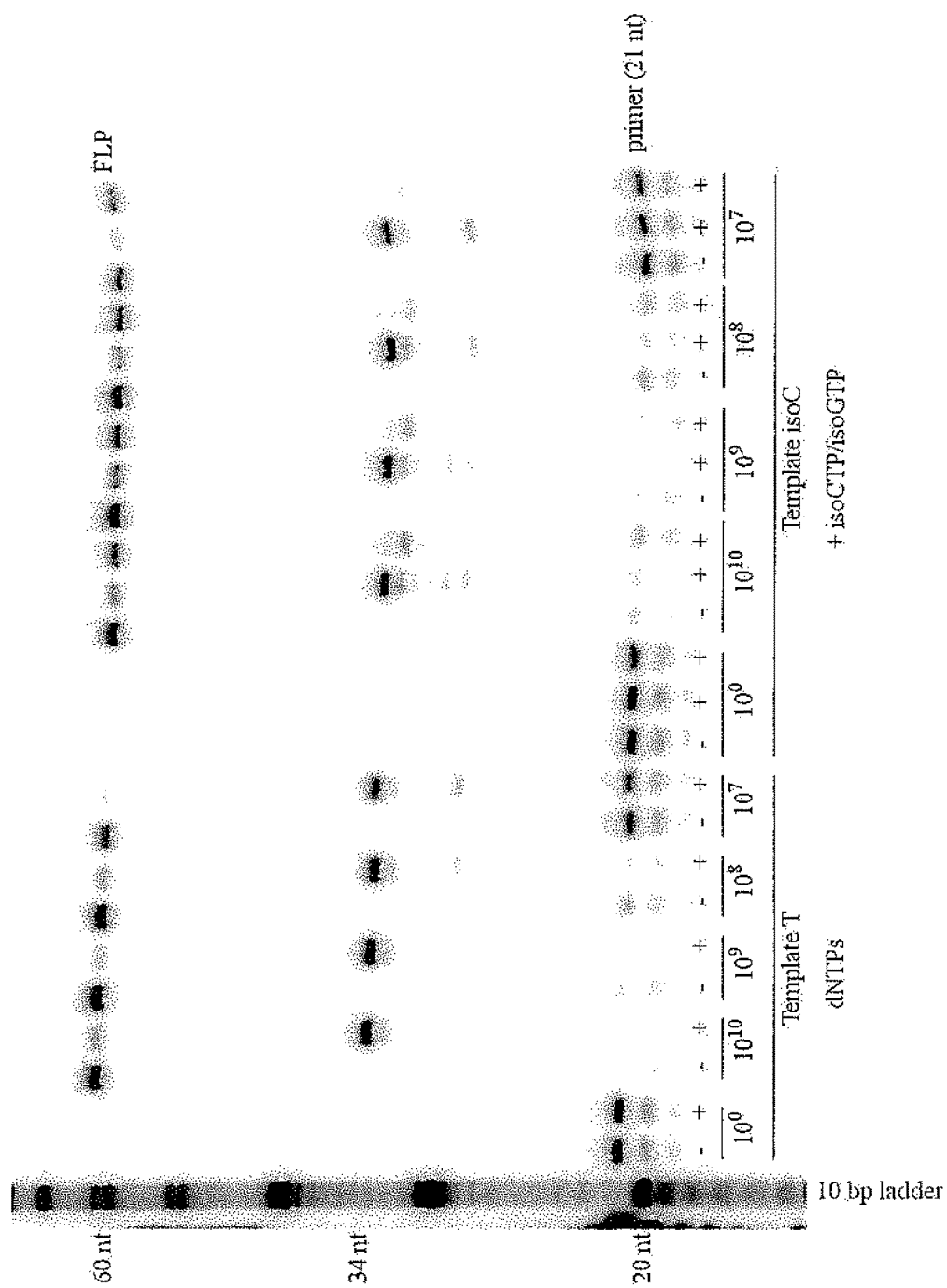
FIG. 4: PAGE (16%) showing PCR amplification of decreasing amounts of template molecules containing a T or isoG using standard dNTPs with the T template and adding, MeisoCTP/isoGTP with the isoG template. Samples are loaded such that the [−/+] indicates [−treatment/+BglII digestion]; the [−/+/+] indicates [−treatment/+BglII digestion/+acid hydrolysis]. Only the isoC template PCRs were subjected to acid hydrolysis. Full length product (FLP) is 60 nt, the digestion product is 34 nucleotides and the primer is 21 nucleotides.
Figure 5:
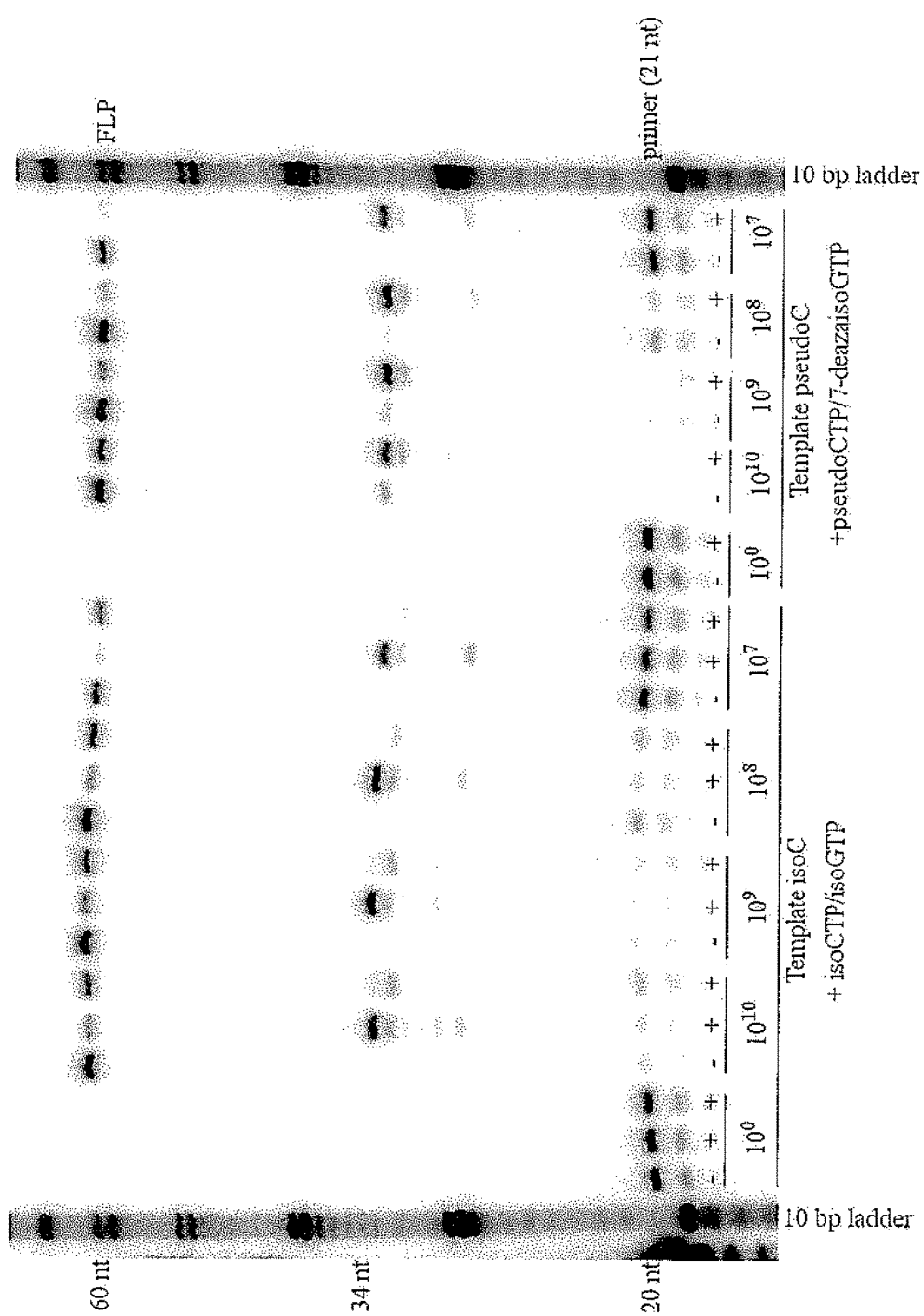
FIG. 5: PAGE (16%) showing PCR amplification of decreasing amounts of template molecules containing an isoC or pseudoC using standard dNTPs with MeisoCTP/isoGTP or with pseudoCTP/7-deazaisoGTP. Samples are loaded so that the [−/+/+] indicates [−treatment/+BglII digestion/+acid hydrolysis] and the [−/+] indicates [−treatment/+BglII digestion]. Only the MeisoC template PCRs were subjected to acid hydrolysis. Full length product (FLP) is 60 nt, the digestion product is 34 nucleotides and the primer is 21 nucleotides.
Figure 6:
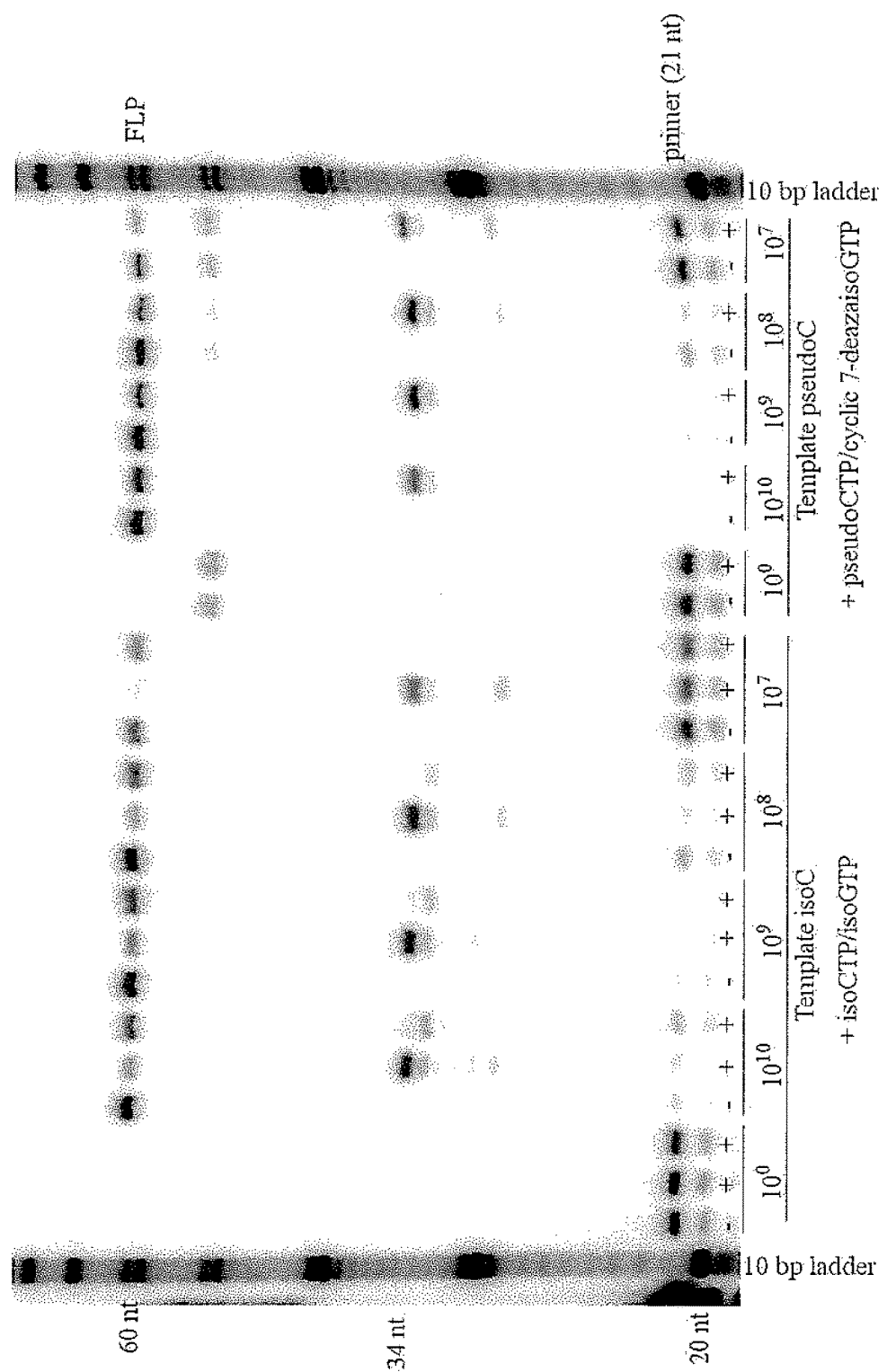
FIG. 6: PAGE (16%) showing PCR amplification of decreasing amounts of template containing a MeisoC or MepseudoC using standard dNTPs with MeisoCTP/isoGTP or with MepseudoCTP/cyclic 7-deazaisoGTP. Samples are loaded such that the [−/+/+] indicates [−treatment/+BglII digestion/+acid hydrolysis] and the [−/+] indicates [−treatment/+BglII digestion]. Only the isoC template PCRs were subjected to acid hydrolysis. Full length product (FLP) is 60 nt, the digestion product is 34 nucleotides and the primer is 21 nucleotides.

PCRs contained, in a 50 μL reaction volume, forward (32P-labeled) and reverse primers (1 pmol each; $6 \times 10^{11}$ molecules), various concentrations of template (10-fold dilutions of $10^{10}$ molecules to $10^7$ molecules), 10 mM bis-tris-propane-HCl, 40 mM potassium acetate, 2 mM MgCl$_2$, 0.1 mg/mL bovine serum albumin, 100 μM of appropriate triphosphates and titanium Taq (1×, Clontech). PCR cycles included an initial denaturation of 2 min 95° C. to activate the hot-start enzyme. Reactions were cycled (30 rounds) at 95° C. 45 sec, 45° C. for 40 sec and 72° C. for 1.5 min. Following PCR, isoG/isoC reactions were treated with an equal volume of 0.1 M acetic acid and incubated at 95° C. for 30 min, tubes were opened and volatiles were allowed to evaporate for 1 min at 95° C. Reactions were cooled on ice, then two volumes of ammonium hydroxide (0.1 M) were added and incubated at 95° C. for 5 min. The ammonium hydroxide was then allowed to evaporate and the mixtures were quenched by the addition of gel loading buffer (10 mM EDTA, 1 mg/mL bromophenol blue, 1 mg/mL xylene cyanol FF, 98% formamide). An aliquot of all the PCRs were digested with BglII (5 units) in NEBuffer 3.1 for 2 hours at 37° C., reactions were quenched by the addition of gel loading buffer and all samples were analyzed by denaturing PAGE (16%). Results are summarized in FIGS. 4-6 and Tables 1-3.

TABLE 2

Figure 2A:
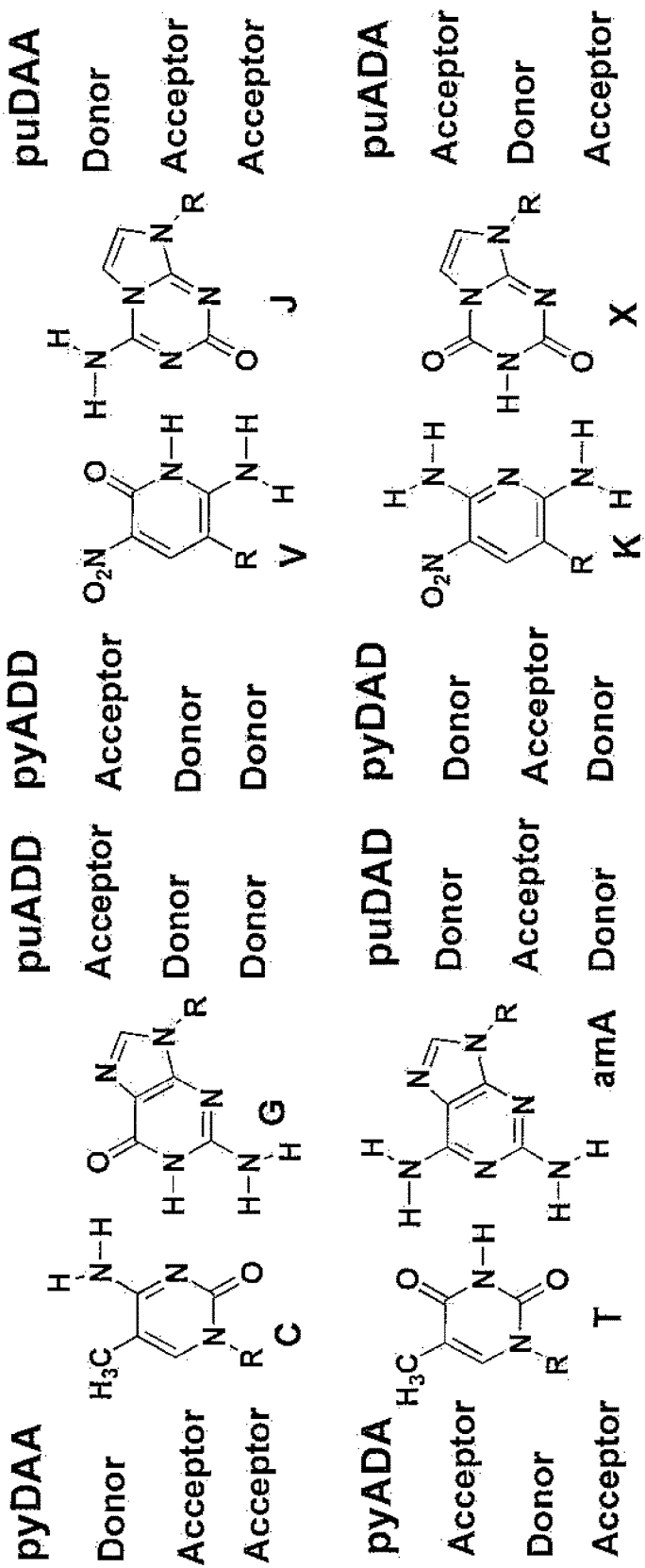
FIG. 2A. The presently preferred embodiments of the non-standard AEGIS nucleobases and their pairs. These have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. Electron density presented to the minor groove is shown by the shaded lobes. Note that some non-standard pyrimidines do not present this density.
Figure 2B:
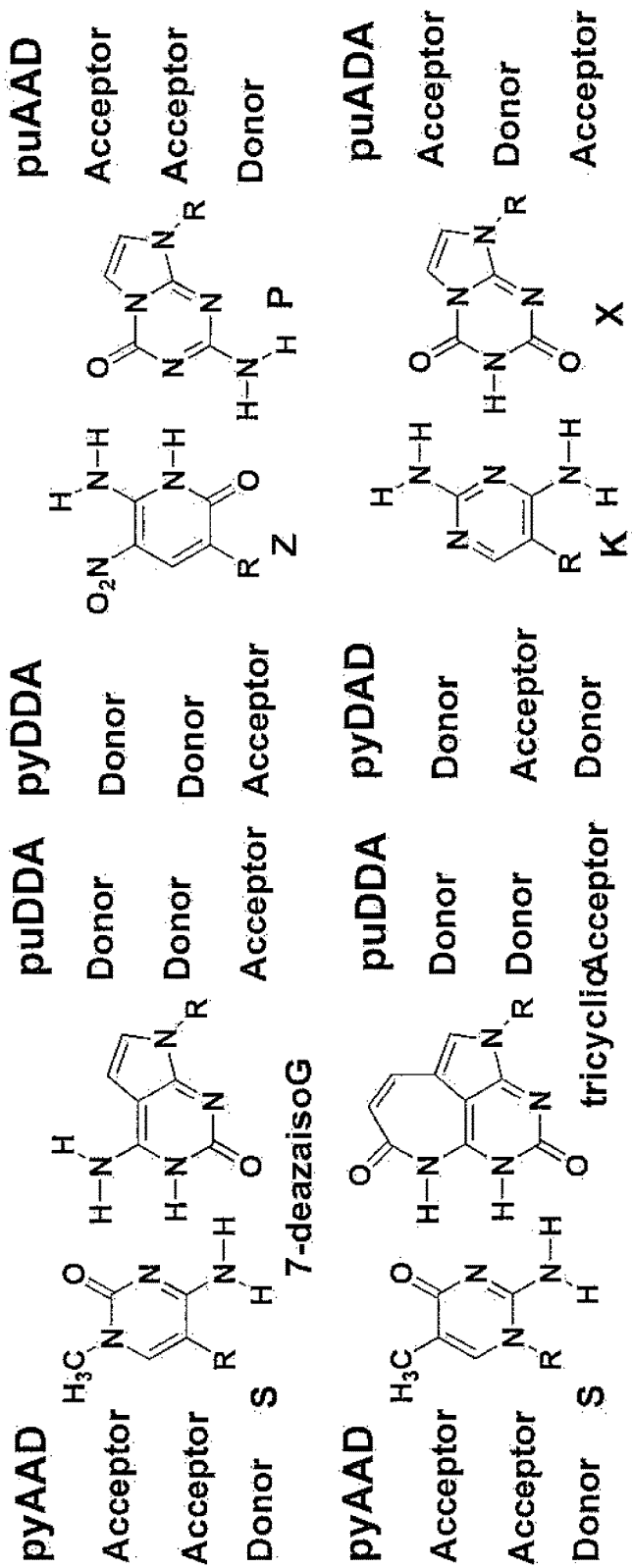
FIG. 2B. The presently preferred embodiments of the non-standard AEGIS nucleobases and their pairs. These have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. Electron density presented to the minor groove is shown by the shaded lobes. Note that some non-standard pyrimidines do not present this density.

Volume of full length product, BglII digested and acid
hydrolyzed product from PCRs seen in FIG. 2 were quantified

| | Template molecules | [1]Theoretical rounds (n) | | [3]Volume (CNT * mm$^2$) | % digested or cleaved |
|---|---|---|---|---|---|
| Template isoC isoC/isoG | $6 \times 10^{10}$ | 3.32 | [2]FLP | 15704 | 84 |
| | | | BglII digested | 80552 | |
| | | | FLP | 45139 | 20 |
| | | | cleaved | 11314 | |
| | $6 \times 10^9$ | 6.64 | FLP | 26608 | 76 |
| | | | BglII digested | 85676 | |
| | | | FLP | 59979 | 9 |
| | | | cleaved | 5895 | |
| | $6 \times 10^8$ | 9.97 | FLP | 15103 | 86 |
| | | | BglII digested | 91069 | |
| | | | FLP | 58601 | 4 |
| | | | cleaved | 2522 | |
| | $6 \times 10^7$ | 13.29 | FLP | 1939 | 96 |
| | | | BglII digested | 46684 | |
| | | | FLP | 23846 | 4 |
| | | | cleaved | 1016 | |
| Template pseudoC pseudoC/7-deazaisoG | $6 \times 10^{10}$ | 3.32 | FLP | 62103 | 46 |
| | | | BglII digested | 53115 | |
| | $6 \times 10^9$ | 6.64 | FLP | 23071 | 80 |
| | | | BglII digested | 95107 | |
| | $6 \times 10^8$ | 9.97 | FLP | 7048 | 94 |
| | | | BglII digested | 102723 | |
| | $6 \times 10^7$ | 13.29 | FLP | 943 | 98 |
| | | | BglII digested | 44840 | |

TABLE 3

Amounts of full-length product, BglII digested and acid hydrolyzed product from PCRs seen in FIG. 3 were quantified

| | Template molecules | [1]Theoretical rounds (n) | | [3]Volume (CNT * mm$^2$) | % digested or cleaved |
|---|---|---|---|---|---|
| Template isoC isoC/isoG | $6 \times 10^1$ | 3.32 | [2]FLP | 23223 | 80 |
| | | | BglII digested | 95848 | |
| | | | FLP cleaved | 56884 16649 | 23 |
| | $6 \times 10^9$ | 6.64 | FLP | 33775 | 76 |
| | | | BglII digested | 105889 | |
| | | | FLP cleaved | 72517 9082 | 11 |
| | $6 \times 10^8$ | 9.97 | FLP | 20336 | 85 |
| | | | BglII digested | 112120 | |
| | | | FLP cleaved | 68412 4783 | 7 |
| | $6 \times 10^7$ | 13.29 | FLP | 4299 | 92 |
| | | | BglII digested | 51836 | |
| | | | FLP cleaved | 31101 2401 | 7 |
| Template pseudoC pseudoC/ cyclic 7-deazaisoG | $6 \times 10^{10}$ | 3.32 | FLP | 95674 | 34 |
| | | | BglII digested | 49236 | |
| | $6 \times 10^9$ | 6.64 | FLP | 60572 | 57 |
| | | | BglII digested | 80051 | |
| | $6 \times 10^8$ | 9.97 | FLP | 48010 | 66 |
| | | | BglII digested | 91204 | |
| | $6 \times 10^7$ | 13.29 | FLP | 14588 | 71 |
| | | | BglII digested | 35225 | |

Example 3

PCR Amplification of Oligonucleotides Containing the Pair Between 6-amino-5-nitro-3-(1'-β-D-2'-deoxyribo-furanosyl)-2(1H)-pyridone and 2-amino-8-(1'-β-D-2'-deoxyribofuranosyl)-imidazo[1,2-a]-1,3,5-triazin-4(8H)-one (the Z:P Pair)

Various polymerases were challenged to incorporate consecutive non-standard nucleotides opposite consecutive non-standard Z and P components in 1× Thermopol reaction buffer (for Taq and Deep Vent (exo$^+$), pH 8.0, measured at room temperature) or 1× Phusion HF buffer (for Phusion at pH ca. 8.3) at 72° C. for the times indicated on the gels (1 to 16 min). Note: the failure of the polymerase to generate full length products in the absence of dZTP and/or dPTP is evidence that no substantial amounts of standard nucleotides are incorporated opposite non-standard template nucleotides.

Negative control (−): dNTPs (each 0.1 mM).
Positive control (+): dNTPs (each 0.1 mM) and dZTP (0.1 mM, left) or dPTP (0.1 mM, right).

Figure 7A:
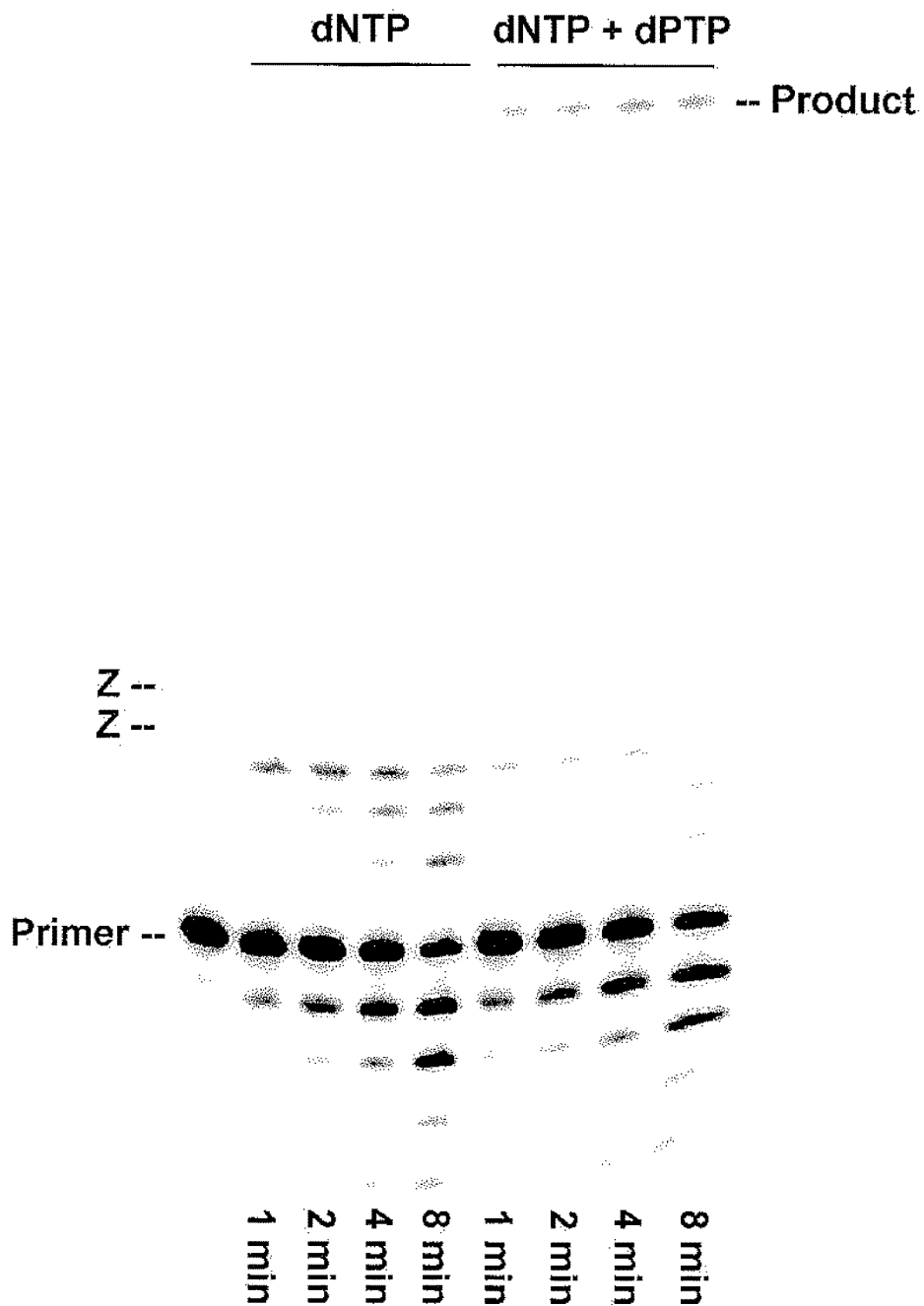
FIG. 7A. PAGE gels showing, from Example 3, PCR amplification of DNA duplexes containing two consecutive non-standard Z:P pairs. Left panel shows PCR with two units of Deep Vent (exo+). Right panel shows PCR with one unit of Deep Vent (exo+).
Figure 7B:
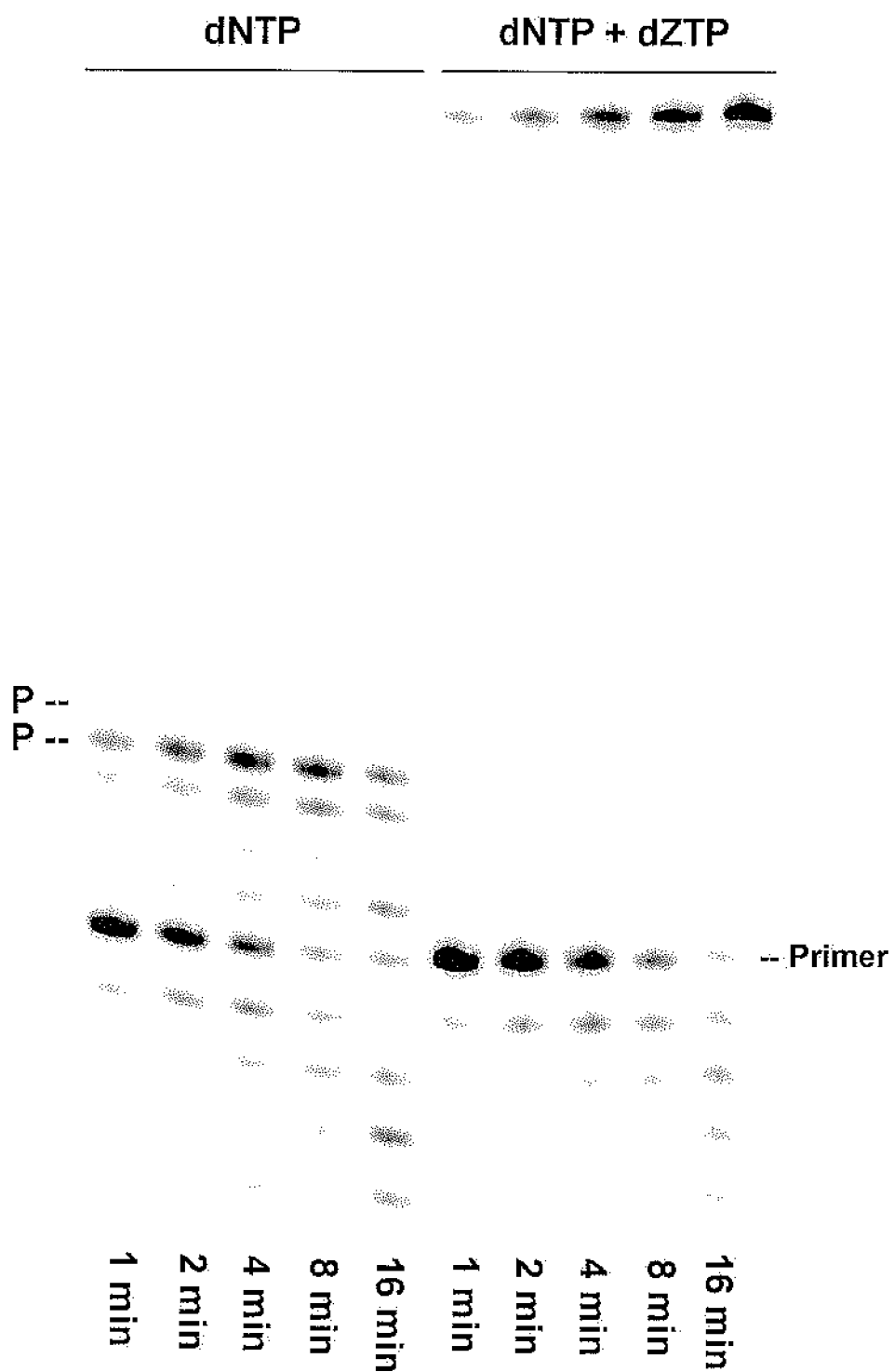
FIG. 7B. PAGE gels showing, from Example 3, PCR amplification of DNA duplexes containing two consecutive non-standard Z:P pairs. Left panel shows PCR with two units of Deep Vent (exo+). Right panel shows PCR with one unit of Deep Vent (exo+).
Figure 8A:
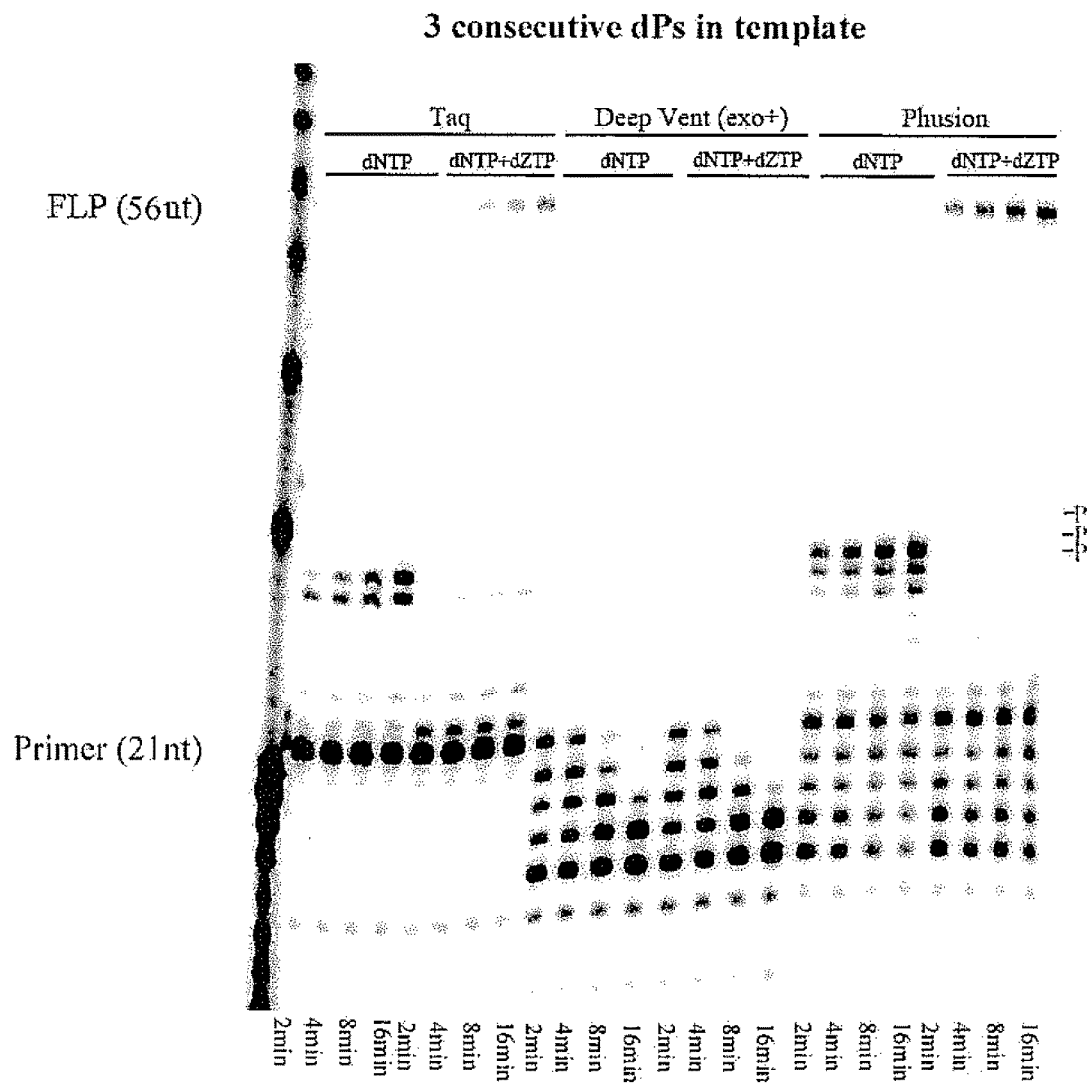
FIG. 8A. PAGE gels showing, from Example 3, PCR amplification of DNA duplexes containing three consecutive non-standard Z:P pairs. Polymerases are as indicated.
Figure 8B:
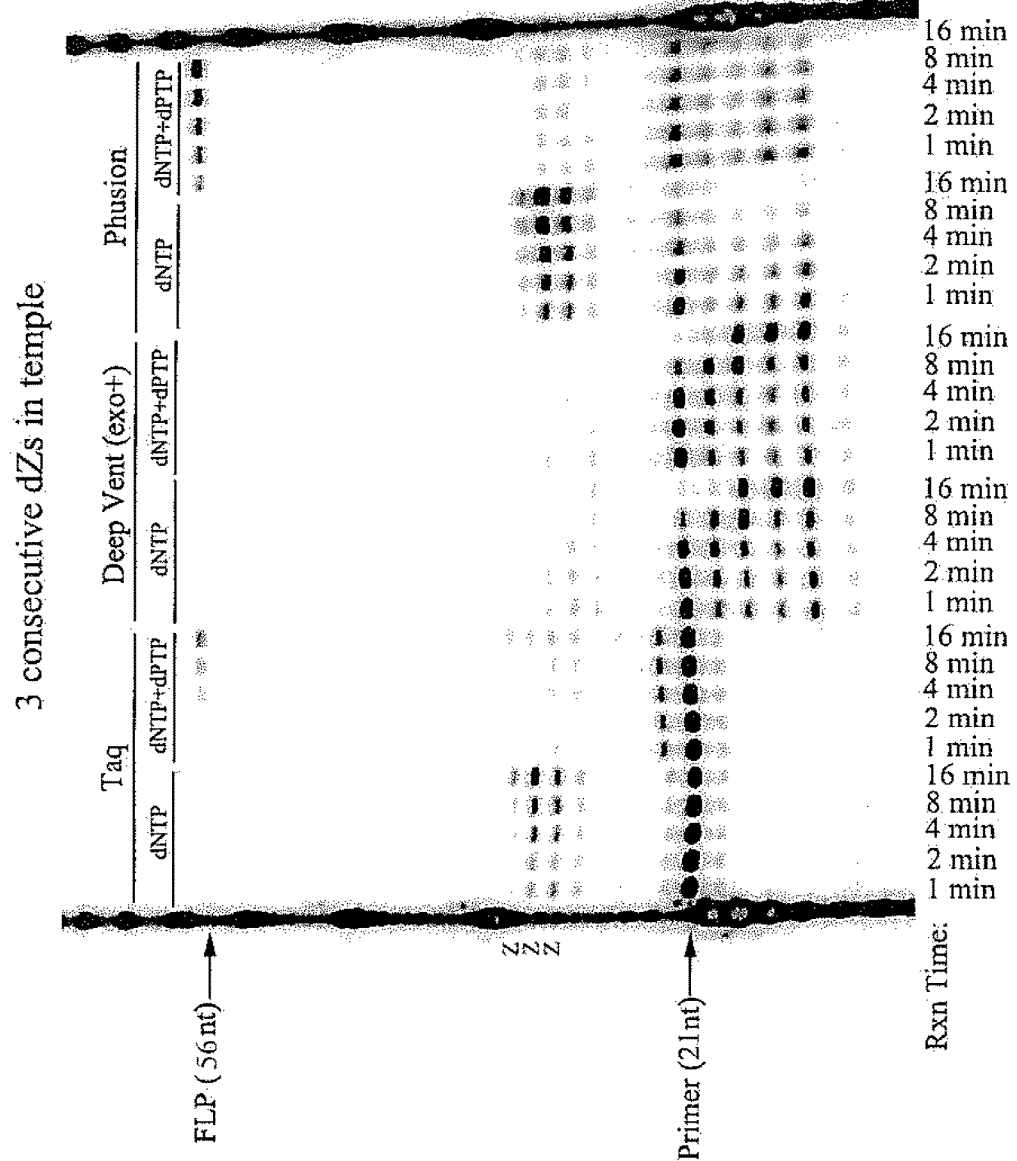
FIG. 8B. PAGE gels showing, from Example 3, PCR amplification of DNA duplexes containing three consecutive non-standard Z:P pairs. Polymerases are as indicated.
Figure 9A:
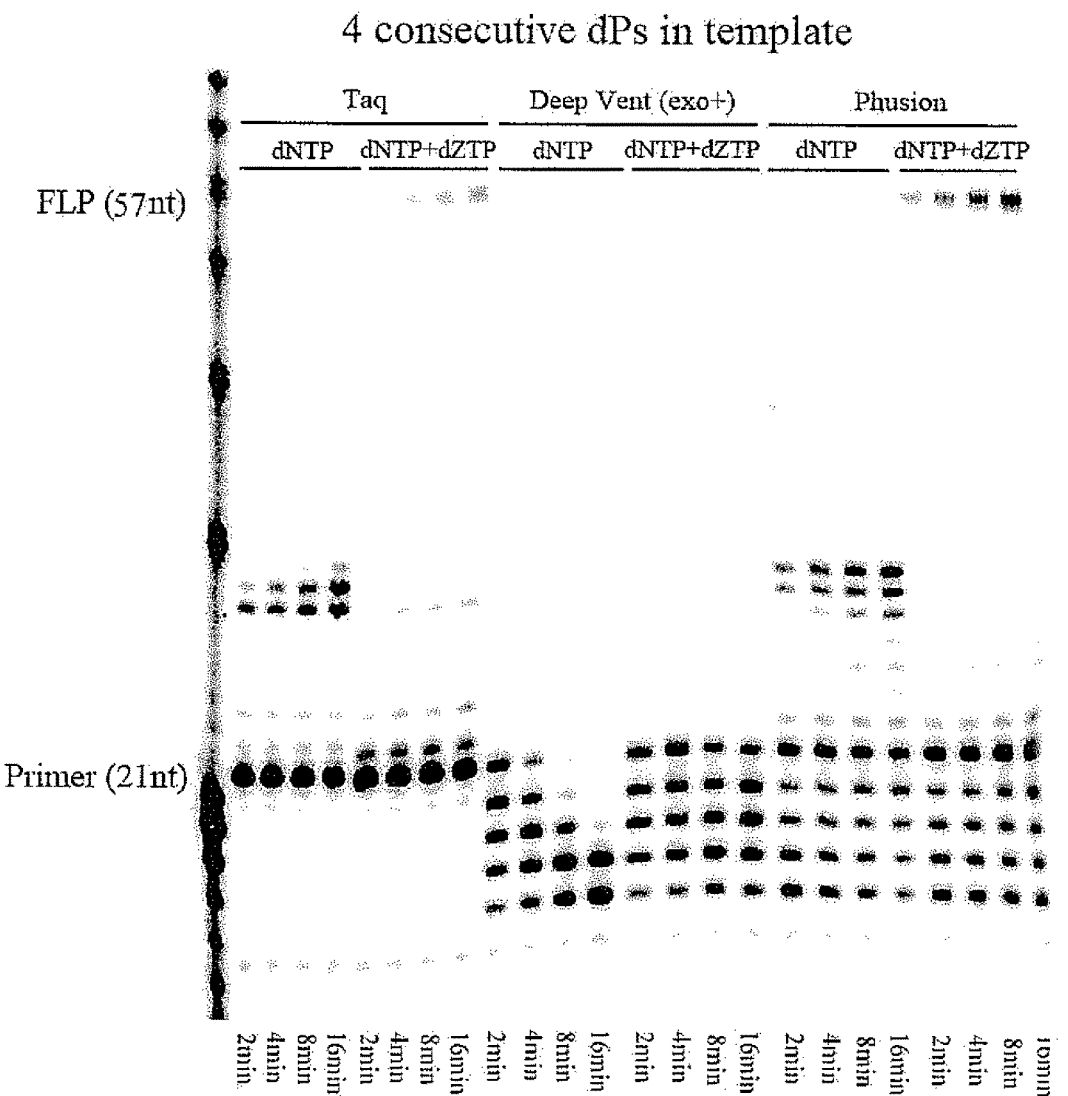
FIG. 9A. PAGE gels showing, from Example 3, PCR amplification of DNA duplexes containing four consecutive non-standard Z:P pairs. Polymerases are as indicated.
Figure 9B:
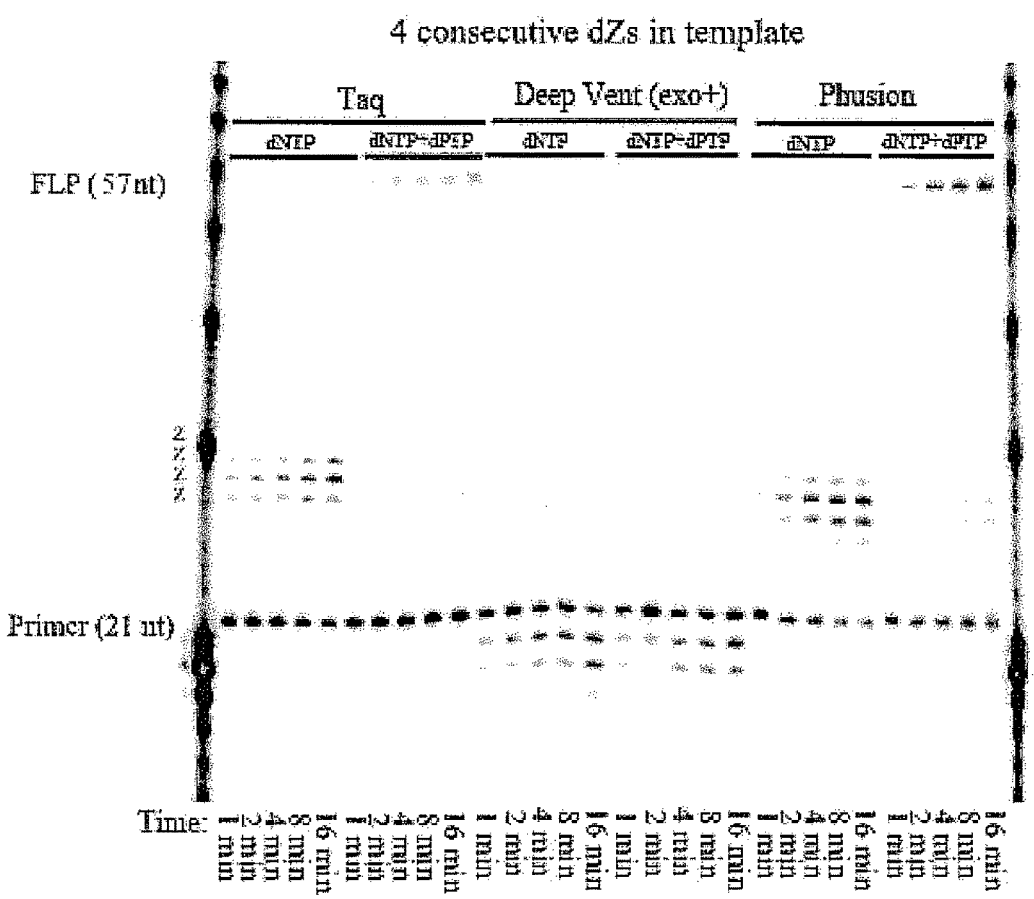
FIG. 9B. PAGE gels showing, from Example 3, PCR amplification of DNA duplexes containing four consecutive non-standard Z:P pairs. Polymerases are as indicated.

(a) Results from two consecutive non-standard nucleotides with Deep Vent (exo$^+$) DNA polymerase (FIG. 7).
(b) Results from three consecutive non-standard nucleotides with Taq, Deep Vent (exo$^+$) and Phusion DNA polymerases (FIG. 8)
(c) Results from four consecutive non-standard nucleotides with Taq, Deep Vent (exo$^+$) and Phusion DNA polymerase (FIG. 9).

Primer-F1:
SEQ ID NO 10
3'-GAAAT*CACTCCCAATTAAGCG-5'

2P-Temp:
SEQ ID NO 11
5'-GCGTAATACGACTCACTATAGACGAPPCTA<u>CTTTAGTGAGGGT</u><u>TAATT</u><u>CGC</u>-3'

2Z-Temp:
SEQ ID NO 12
3'-<u>CGCATTATGCTGAGTGATATCTGCT</u>ZZGATGAAATCACTCCCAATTAAGCG-5'

Primer-R1:
SEQ ID NO 13
5'-GCGTAATACGACTCAC*TATAG-3'

Primer-F1:
SEQ ID NO 14
3'-GAAAT*CACTCCCAATTAAGCG-5'

3P-Temp:
SEQ ID NO 15
5' GCGTAATACGACTCACTATAGACACTPPPTACTCA<u>CTTTAGTGAGGGT</u><u>TAATTCGC</u>-3'

3Z-Temp:
SEQ ID NO 16
3'-<u>CGCATTATGCTGAGTGATATCTGTGA</u>ZZZATGAGTGAAATCACTCCCAATTAAGCG-5'

Primer-R1:
SEQ ID NO 17
5'-GCGTAATACGACTCAC*TATAG-3'

Primer-F1:
SEQ ID NO 18
3'-GAAAT*CACTCCCAATTAAGCG-5'

4P-Temp:
SEQ ID NO 19
5'-GCGTAATACGACTCACTATAGACACTPPPPTACTCA<u>CTTTAGTGAGGG</u><u>TTAATTCGC</u>-3'

4Z-Temp:
SEQ ID NO 20
3'-<u>CGCATTATGCTGAGTGATATCTGTGA</u>ZZZZATGAGTGAAATCACTCCCAATTAAGCG-5'

Primer-R1:
SEQ ID NO 21
5'-GCGTAATACGACTCAC*TATAG-3'

Polymerase Extension that Reads Through Multiple Consecutive Non-Standard Nucleobases 5'-$^{32}$P-Labeled primer (Primer-F1 or Primer-R1, 0.2 pmole of hot primer plus 4 pmole of cold primer, final concentration 70 nM) was annealed to a template containing multiple consecutive non-standard nucleobases (P or Z, 6 pmole, final concentration 100 nM) in 1× ThermoPol polymerase reaction buffer (pH=8.0 at room temperature) or 1× HF Phusion buffer (pH=8.3 at room temperature) by heating at 96° C. for 5 min and then slow cooling (0.5 h) to room temperature. dNTPs (final 0.1 mM for each) or both dNTPs and dZ(P)TP (final 0.1 mM for each) were added at room temperature. The reaction mixture was pre-heated at 72° C. for 30 seconds. Extension was initiated by adding Taq (2.5 units), Deep Vent (exo$^+$, 1 unit for Figure S1 (a) right panel and 2 units for the rest of Figure S1), or Phusion (1 unit) DNA polymerase to give a final volume of 60 µl. The primer was extended at 72° C. and aliquots (7 µl) were taken from each reaction at time intervals (1, 2, 4, 8, and 16 min), quenched by PAGE loading/quench buffer (10 µL, 10 mM EDTA in formamide). Samples were resolved by electrophoresis using a 16% PAGE (7 M urea). The gel was analyzed using MolecularImager software (FIGS. 7-9).

Measuring the Retention and Mutation of Z:P Pair in Optimized Six-Letter PCR

In 1× ThermoPol reaction buffer (pH 8.0 measured at 25° C.), synthetic template (Bsp-P, Table 1) or standard template (Bsp-G, Table 1) was amplified (1000 to 100000 fold, respectively) using JumpStart Taq DNA polymerse (0.08 unit/µl, Sigma) with primers (Primer-F3 and Primer-R3) and dZTP=0.05 mM, dPTP=0.6 mM, dA,T,G/TPs=0.1 mM, dCTP=0.2 mM, or 0.4 mM, or 0.6 mM. The PCR mixture were cycled using the following conditions: one cycle of 95° C. for 1 min; followed by 31 cycles of (95° C. for 30 s, 55° C. for 30 s, 72° C. for 1 min); and finally 72° C. for 10 min. Upon the completion of PCR amplification, 1 µl of PCR mixture was digested with BsP120I (0.5 µl, final 0.5 units/µl) in 1× Buffer B at 37° C. for 20 hours (10 µl of reaction volume). Additional 0.5 µl of Bsp120I was added to the digestion mixture and incubated for another 20 hours. The digestion products were resolved on 10% PAGE gel (7 M urea) and visualized by autoradiography.

PCR Amplification of the GACTZP DNA and Sequencing of the PCR Products

Synthetic GACTZP DNA containing various numbers of Z and P nucleotides incorporated at various positions, adjacent and spaced apart (final 0.04 nM of each) were amplified in 1× ThermoPol reaction buffer (pH=8.0, measured at room temperature) containing primers (0.4 µM each of Primer-F1 and Primer-R1, or Primer-F2 and Primer-R2, or Primer-F3 and Primer-R3), dA,T,G/TPs (each 0.1 mM), dCTP (0.2 mM), dZTP (0.05 mM), dPTP (0.6 mM), and 0.05 unit/µl of JumpStart Taq DNA polymerase in a total volume of 50 µl. The following PCR conditions were used: one cycle of 95° C. for 1 min; followed by 21 cycles of (95° C. for 20 s, 58° C. for 25 s, 72° C. for 3 min); and finally 72° C. for 10 min. Upon the completion of the PCR, samples (10 µl) were taken from each PCR mixture, mixed with 6× agarose loading dye (2 µl, Promega), and analyzed on agarose gel.

A sample (20 µl) of PCR mixture taken from the above PCR was mixed with 8 µl of ExoSAP-IT (USB, Cleveland, Ohio) and incubated at 37° C. for 30 min to degrade remaining primers and nucleotides, then, incubated at 80° C. for 15 min. The mixture was purified by Qiaquick Nucleotide Remove Kit (Qiagen, Valencia, Calif.). The GACTZP DNA was eluted from the spin column using EB buffer (200 µl, 10 mM TrisCl, pH 8.5).

Example 4

Figure 10:
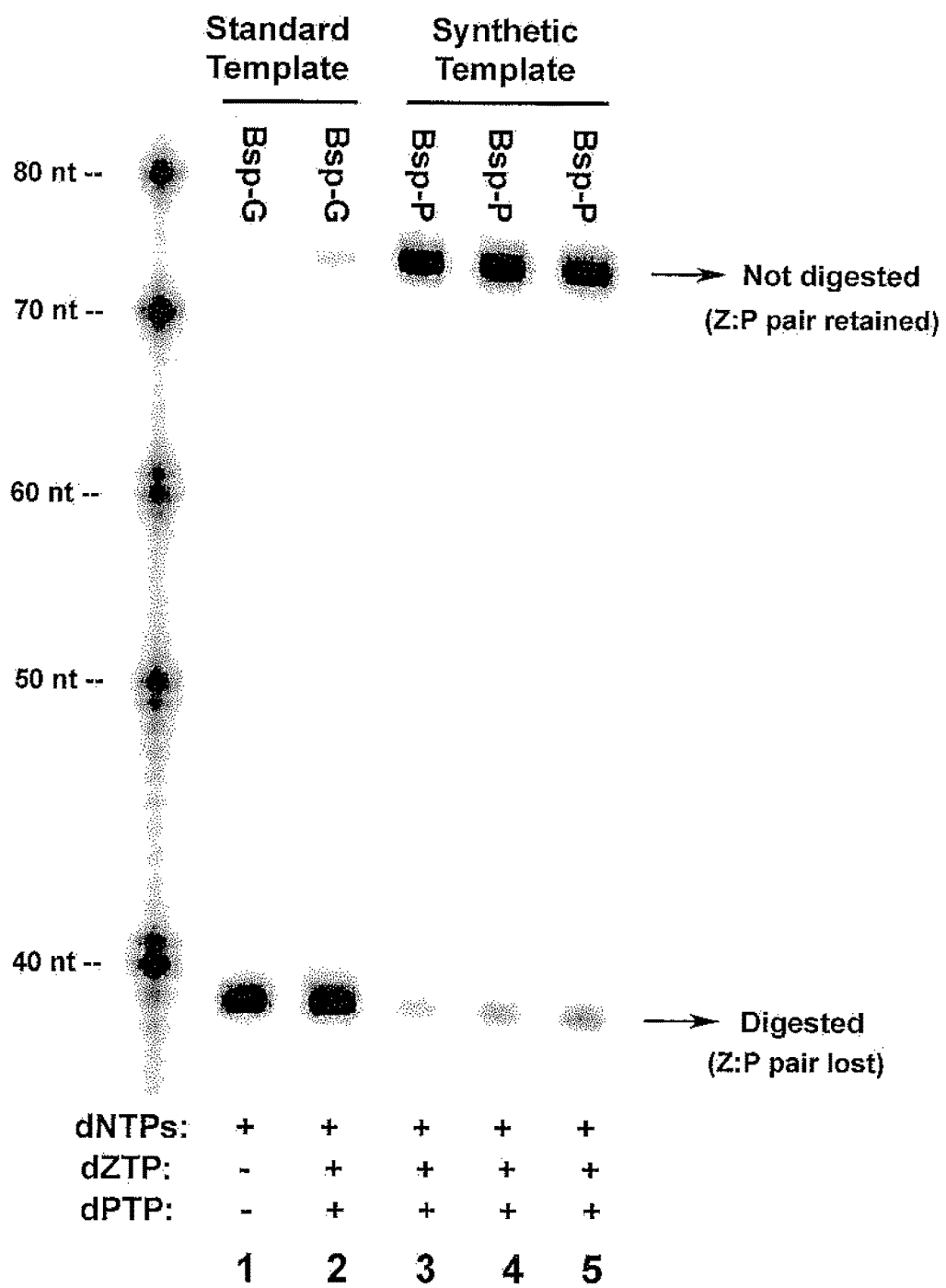
FIG. 10. PAGE gels showing, from Example 4, PCR of DNA duplexes containing Z:P pairs. (a) Standard template (Bsp-G) and AEGIS template (Bsp-P) amplified with Taq polymerase in 1× ThermoPol buffer (pH 8.0), followed by digestion with Bsp120I. Four standard dNTPs (each 0.2 mM), dZTP=0.2 mM, and dPTP=0.2 mM. Extent of digestion equals extent of loss, proving "useful PCR". Lanes 1 and 2: Standard template amplified $10^4$ fold using Taq, without (lane 1) and with (lane 2) dZTP and dPTP; Lanes 3, 4, and 5: Synthetic template, $10^3$ (lane 3), $10^4$ (lane 4), and $10^5$ (lane 5) fold amplification, with dZTP and dPTP; Not digested: indicates fraction of PCR product retaining Z:P pair, resisting Bsp120I digestion; Digested: indicates fraction of PCR product digested. The retention rate of Z:P pair is ca. 99.2% per theoretical PCR cycle; the gain of Z:P pair in the sequence is ~0.6% per theoretical cycle. (b) Standard template (Bsp-G, Table 1) and AEGIS template (Bsp-P, Table 1) were amplified using Taq DNA polymerase in 1× ThermoPol buffer (pH 8.0), followed by digestion with Bsp120I. dNTPs indicates dA,T,G/TPs (each 0.1 mM), dZTP=0.05 mM, dPTP=0.6 mM, and various dCTP concentration (0.2 mM, 0.4 mM, or 0.6 mM). Lane 1 and 2: Standard template was amplified $10^4$ fold using Taq, without (lane 1) and with (lane 2) dZTP and dPTP; Lane 3, 4, and 5: Synthetic template, $10^3$ (lane 3), $10^4$ (lane 4), and $10^5$ (lane 5) fold amplification, with both dZTP and dPTP; Not digested: indicates the fraction of PCR product retained Z:P pair, therefore, resisted endonuclease digestion; Digested: indicates the fraction of PCR product was digested.
Figure 11:
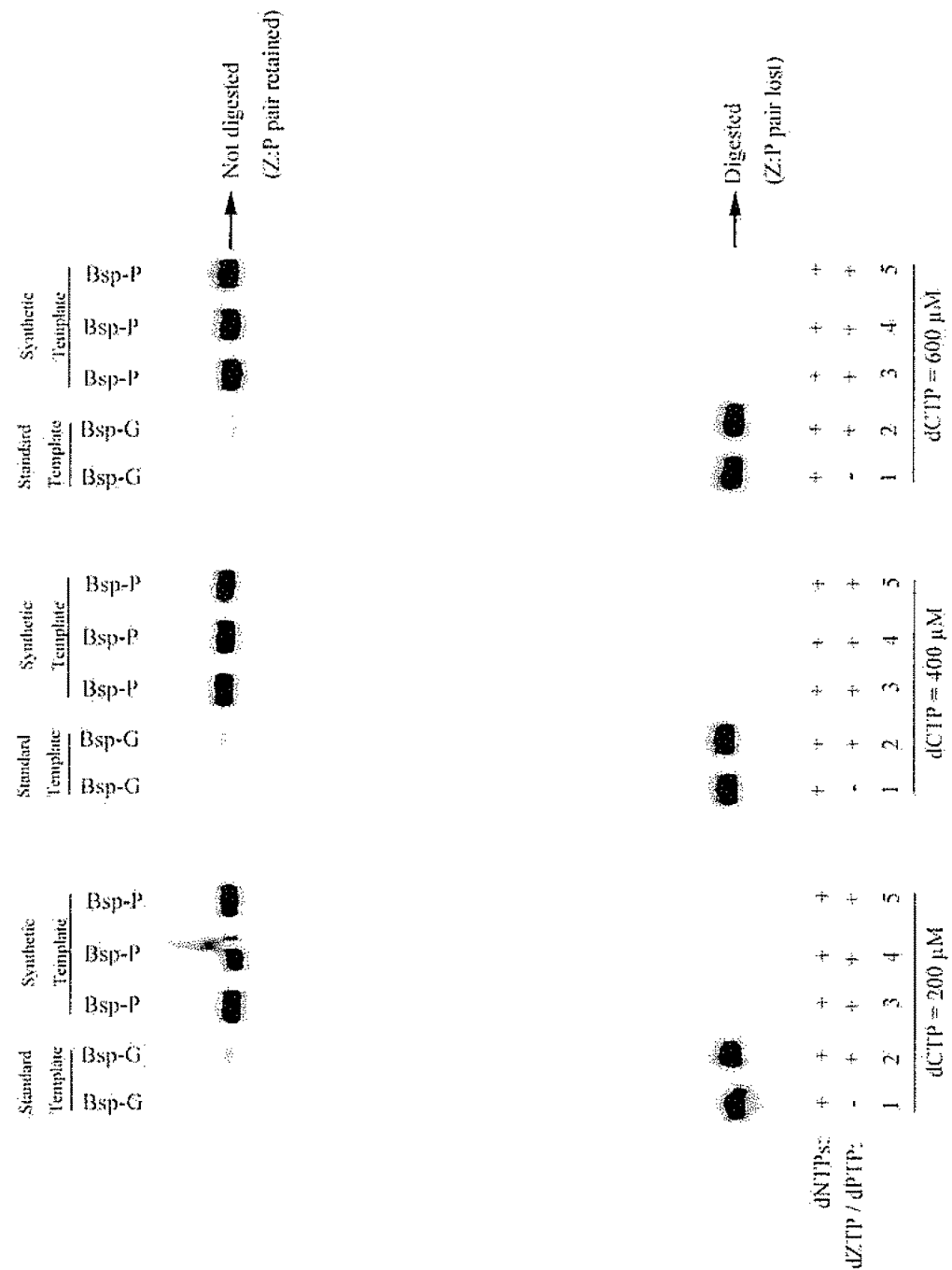
FIG. 11. PAGE gels showing, from Example 5, six-letter PCR under optimized triphosphate concentrations (dZTP=0.05 mM, dPTP=0.6 mM, dA,T,G/TPs=0.1 mM, and dCTP=0.2, 0.4, or 0.6 mM) containing Z:P pairs. Standard template (Bsp-G, Table 1) and synthetic template (Bsp-P, Table 1) were amplified using Taq DNA polymerase in 1× ThermoPol buffer (pH 8.0), followed by digestion with Bsp120I endonuclease. The extent of digestion is equal to the extent of loss after the indicated number of cycles, proving a "useful PCR".

PCR Amplification of GACTZP DNA (FIG. 10)

Under the optimized triphosphate concentrations, the retention rate of Z:P pair and the forward mutation (gain of Z:P pair) in the recognition sequence per theoretical PCR cycle for dCTP=0.2 mM (Left panel) are ca. 99.83% and 0.37%, for dCTP=0.4 mM (Middle panel) are ca. 99.83% and 0.25%, for dCTP=0.6 mM (Right panel) are ca. 99.80% and 0.20%. The following oligonucleotides were used:

Oligonucleotides Used in Six-Letter GACTZP PCR

Primer-F1:
SEQ ID NO 22
3'-GAAATCACTCCCAATTAAGCG-5'

2G-Temp:
SEQ ID NO 23
5'-GCGTAATACGACTCACTATAGACGAGGCTA CTTTAGTGAGGGTTAATT CGC-3'

1P-Temp:
SEQ ID NO 24
5'-GCGTAATACGACTCACTATAGACGAPCGTA CTTTAGTGAGGGTTAATT CGC-3'

2P-Temp:
SEQ ID NO 25
5'-GCGTAATACGACTCACTATAGACGAPPCTA CTTTAGTGAGGGTTAATT CGC-3'

3P-Temp:
SEQ ID NO 26
5'-GCGTAATACGACTCACTATAGACACTPPPTACTCA CTTTAGTGAGGGT TAATTCGC-3'

4P-Temp:
SEQ ID NO 27
5'-GCGTAATACGACTCACTATAGACACTPPPPTACTCA CTTTAGTGAGGG TTAATTCGC-3'

4G-Temp:
SEQ ID NO 28
5'-GCGTAATACGACTCACTATAGACACTGGGGTACTCA CTTTAGTGAGGG TTAATTCGC-3'

2C-Temp:
SEQ ID NO 29
3'-CGCATTATGCTGAGTGATATCTGCTCCGATGAAATCACTCCCAATTAA GCG-5'

1Z-Temp:
SEQ ID NO 30
3'-CGCATTATGCTGAGTGATATCTGCTZGCATGAAATCACTCCCAATTAA GCG-5'

2Z-Temp:
SEQ ID NO 31
3'-CGCATTATGCTGAGTGATATCTGCTZZGATGAAATCACTCCCAATTAA GCG-5'

3Z-Temp:
SEQ ID NO 32
3'-CGCATTATGCTGAGTGATATCTGTGAZZZATGAGTGAAATCACTCCCA ATTAAGCG-5'

4Z-Temp:
SEQ ID NO 33
3'-CGCATTATGCTGAGTGATATCTGTGAZZZZATGAGTGAAATCACTCCC AATTAAGCG-5'

4C-Temp:
SEQ ID NO 34
3'-CGCATTATGCTGAGTGATATCTGTGACCCCATGAGTGAAATCACTCCC AATTAAGCG-5'

Primer-R1:
SEQ ID NO 35
5'-GCGTAATACGACTCACTATAG-3'

Primer-F2:
SEQ ID NO 36
3'-CAGTATCGACAAAGGACACACGCT-5'

-continued

Z2-2P:
SEQ ID NO 37
5'-GACACTAGTAGCACTCACTATACGTGACTCPTCACZZAGTGCPACTAC
GGTCATAGCTGTTTCCTGTGTGCGA-3'

PP-2Z:
SEQ ID NO 38
3'-CTGTGATCATCGTGAGTGATATGCACTGAGZAGTGPPTCACGZTGATG
CCAGTATCGACAAAGGACACACGCT-5'

Primer-R2:
SEQ ID NO 39
5'-GACACTAGTAGCACTCACTATACG-3'

Primer-F3:
SEQ ID NO 40
3'-TATGCAACGCTAGCGAGGAAGGAC-5'

Bsp-Z:
SEQ ID NO 41
5'-CTAGGACGACGGACTGCCTATGAGAGACATGAGGGCCZGGTACCATCG
ATACGTTGCGATCGCTCCTTCCTG-3'

Bsp-P:
SEQ ID NO 42
3'-GATCCTGCTGCCTGACGGATACTCTCTGTACTCCCGGPCCATGGTAGC
TATGCAACGCTAGCGAGGAAGGAC-5'

Bsp-C:
SEQ ID NO 43
5'-CTAGGACGACGGACTGCCTATGAGAGACATGAGGGCCCGGTACCATCG
ATACGTTGCGATCGCTCCTTCCTG-3'

Bsp-G:
SEQ ID NO 44
3'-GATCCTGCTGCCTGACGGATACTCTCTGTACTCCCGGGCCATGGTAGC
TATGCAACGCTAGCGAGGAAGGAC-5'

Primer-R3:
SEQ ID NO 45
5'-CTAGGACGACGGACTGCCTATGAG-3'

Example 5

Figure 12:
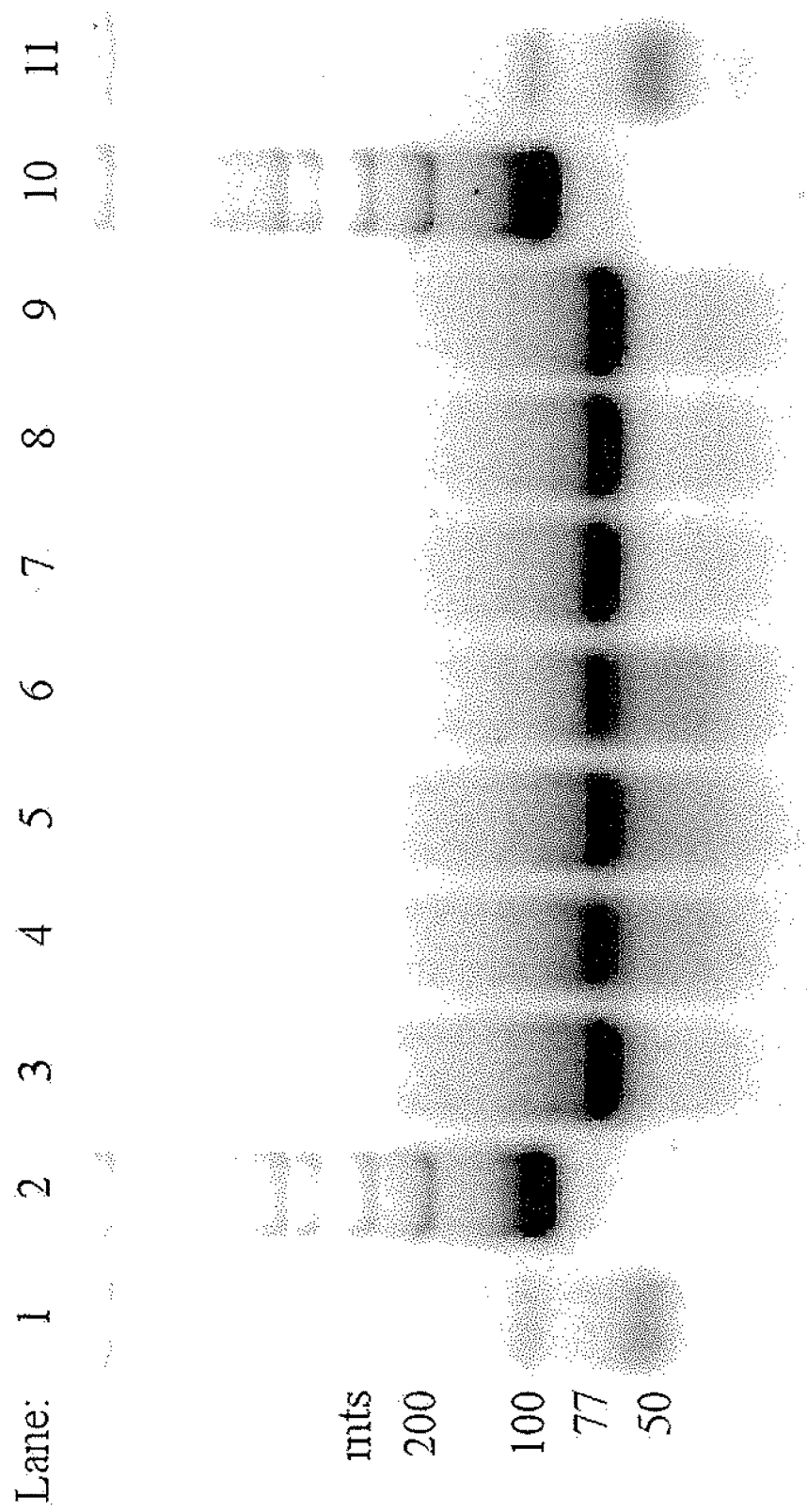
FIG. 12. RNA made by transcribing DNA templates using T7 RNA polymerase resolved on a 3% agarose gel stained with ethidium bromide. Lane 1 and 11, abnova RNA ladder. Lanes 2 and 10, Century RNA ladder. Lane 3 shows product using standard template 01, lanes 4, 5 and 6 show products with Z-containing templates to generate P-containing RNA. Lanes 7, 8, and 9 show products with P-containing templates to generate Z-containing tRNA. Lanes 3-9 contain transcription products using templates 01-07, respectively. The correct size (~77 mts) RNA product is visualized.
Figure 13A:
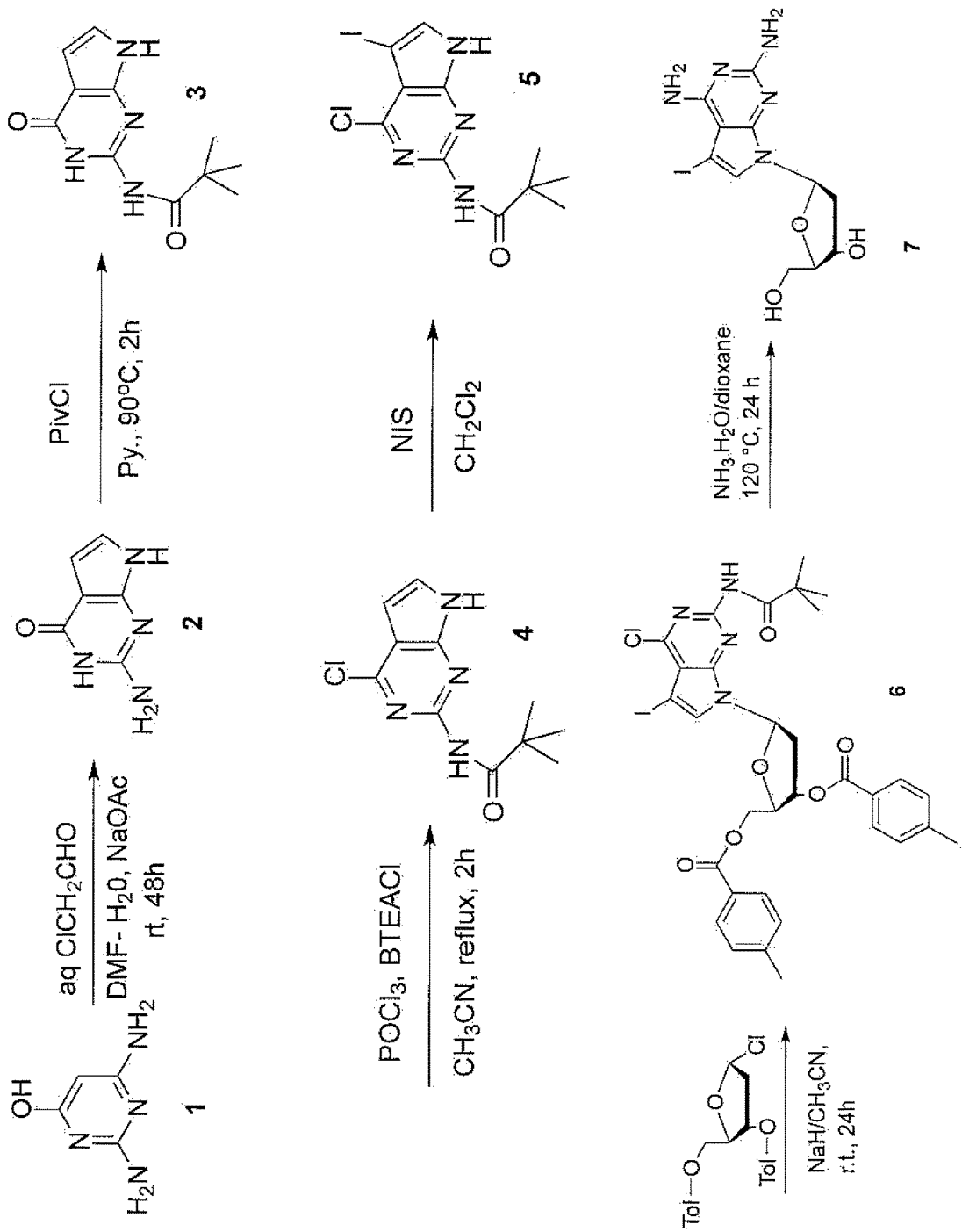
FIG. 13A. Synthesis of tricyclic analog of 7-deazaisoguanosine and its triphosphate.
Figure 13B:
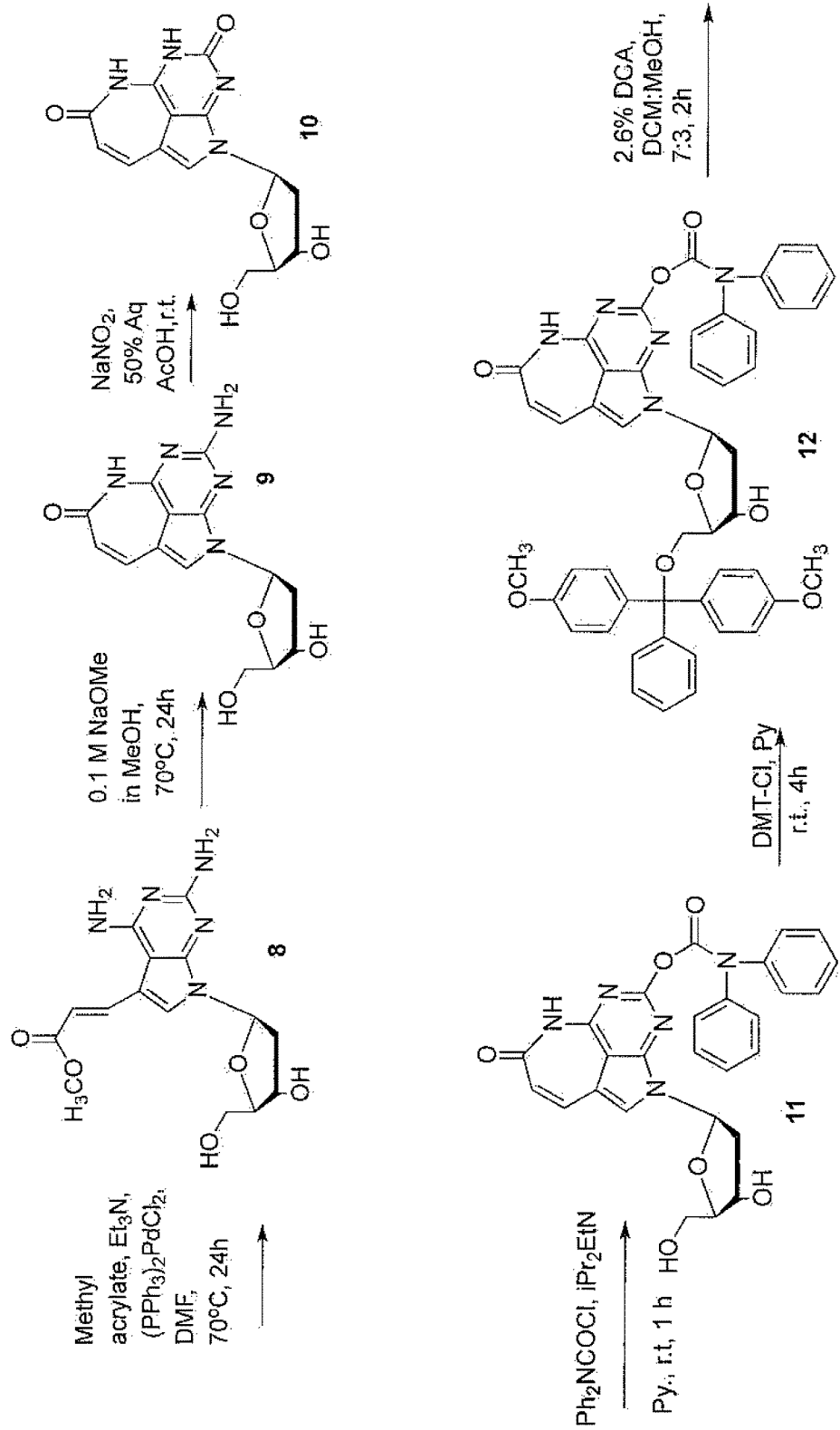
FIG. 13B. Synthesis of tricyclic analog of 7-deazaisoguanosine and its triphosphate.
Figure 13C:
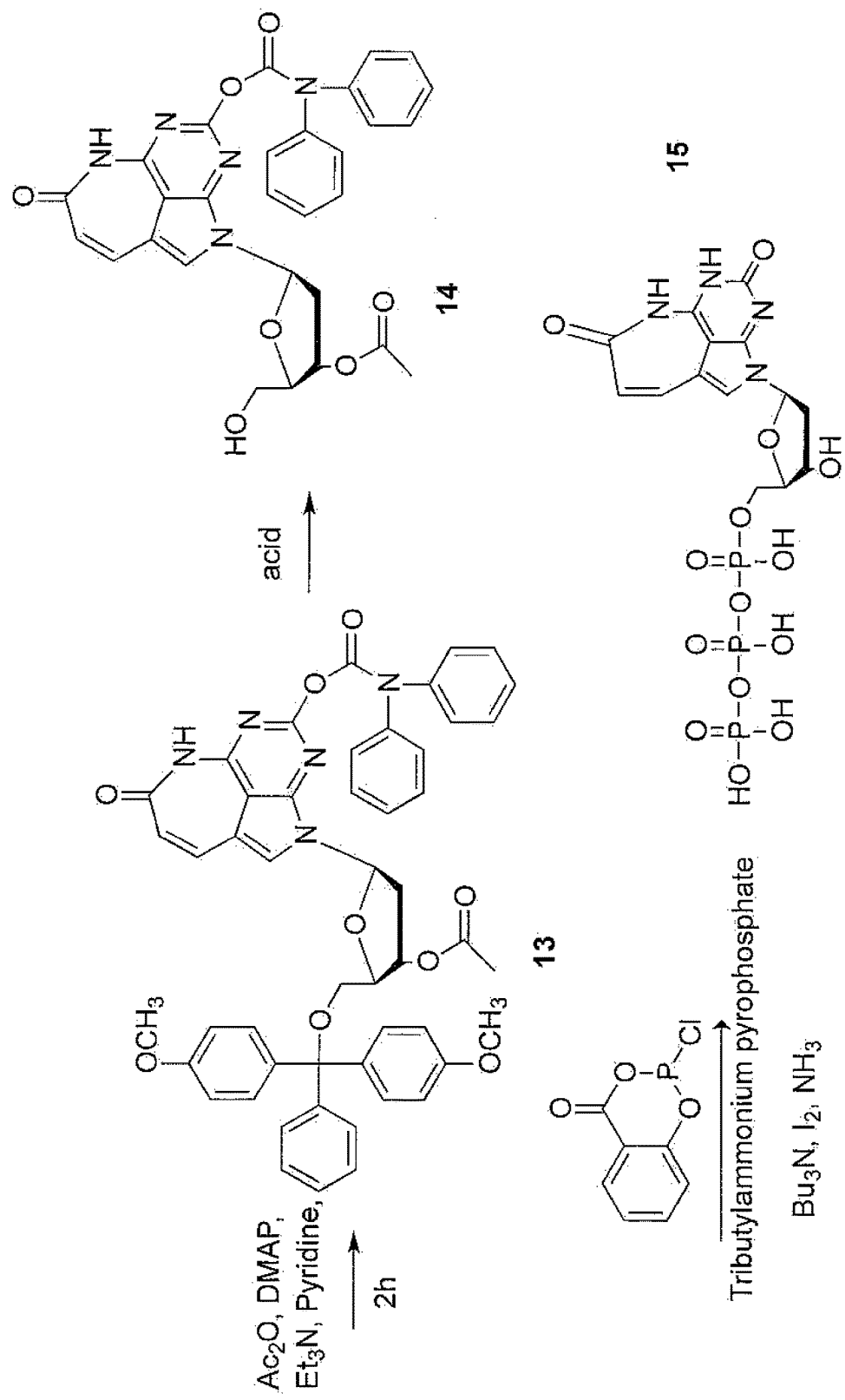
FIG. 13C. Synthesis of tricyclic analog of 7-deazaisoguanosine and its triphosphate.

RNA Synthesis (FIG. 12)

Transcription templates were annealed by independently combining equimolar ratios of appropriate top strand and bottom strands of tDNA templates (01-07, respectively) in 1× transcription buffer (20 mM NaCl, 40 mM Tris pH 7.8, 6 mM MgCl$_2$, 2 mM spermidine, and 10 mM DTT), heating to 85° C. and then cooling to room temperature.

Seven different transcription reactions contained a final concentration of 0.25 μg template DNA (01-07, respectively), in transcription buffer (20 mM NaCl, 40 mM Tris pH 7.8, 16 mM MgCl2, 2 mM Spermidine, and 10 mM DTT), T7 RNA polymerase (4 Unit/μL final) and 2 mM each rNTP. Transcriptions were incubated at 37° C. for 16 hours and were quenched with 3-fold formamide quench buffer. Samples were resolved on a 3% agarose gel (FIG. 12). Small scale transcription reactions using the DNA templates yielded RNA of the appropriate size. The following DNA template sequences were used:

SEQ ID NO 46
5'-GGCGTAATACGACTCACTATAGGCTCTGTAGTTCAGTCGGTAGAACGG
CGGActTCCAATCCGTATGTCACTGGTTCGAGTCCAGTCAGAGCCGCCA

SEQ ID NO 47
3'-CCGCATTATGCTGAGTGATATCCGAGACATCAAGTCAGCCATCTTGCC
GCCTGAAGGTTAGGCATACAGTGACCAAGCTCAGGTCAGTCTCGGCGGT-
5'

SEQ ID NO 48
5'-GGCGTAATACGACTCACTATAGGCTCTGTAGTTCAGTCGGTAGAACGG
CGGACTPCCAATCCGTATGTCACTGGTTCGAGTCCAGTCAGAGCCGCCA

SEQ ID NO 49
3'-CCGCATTATGCTGAGTGATATCCGAGACATCAAGTCAGCCATCTTGCC
GCCTGAZGGTTAGGCATACAGTGACCAAGCTCAGGTCAGTCTCGGCGGT-
5'

SEQ ID NO 50
5'-GGCGTAATACGACTCACTATAGGCTCTGTAGTTCAGTCGGTAGAACGG
CGGACTTPCAATCCGTATGTCACTGGTTCGAGTCCAGTCAGAGCCGCCA

SEQ ID NO 51
3'-CCGCATTATGCTGAGTGATATCCGAGACATCAAGTCAGCCATCTTGCC
GCCTGAAZGTTAGGCATACAGTGACCAAGCTCAGGTCAGTCTCGGCGGT-
5'

SEQ ID NO 52
5'-GGCGTAATACGACTCACTATAGGCTCTGTAGTTCAGTCGGTAGAACGG
CGGACTTCPAATCCGTATGTCACTGGTTCGAGTCCAGTCAGAGCCGCCA

SEQ ID NO 53
3'-CCGCATTATGCTGAGTGATATCCGAGACATCAAGTCAGCCATCTTGCC
GCCTGAAGZTTAGGCATACAGTGACCAAGCTCAGGTCAGTCTCGGCGGT-
5'

SEQ ID NO 54
5'-GGCGTAATACGACTCACTATAGGCTCTGTAGTTCAGTCGGTAGAACGG
CGGACTZCCAATCCGTATGTCACTGGTTCGAGTCCAGTCAGAGCCGCCA

SEQ ID NO 55
3'-CCGCATTATGCTGAGTGATATCCGAGACATCAAGTCAGCCATCTTGCC
GCCTGAPGGTTAGGCATACAGTGACCAAGCTCAGGTCAGTCTCGGCGGT-
5'

SEQ ID NO 56
5'-GGCGTAATACGACTCACTATAGGCTCTGTAGTTCAGTCGGTAGAACGG
CGGACTTZCAATCCGTATGTCACTGGTTCGAGTCCAGTCAGAGCCGCCA

SEQ ID NO 57
3'-CCGCATTATGCTGAGTGATATCCGAGACATCAAGTCAGCCATCTTGCC
GCCTGAAPGTTAGGCATACAGTGACCAAGCTCAGGTCAGTCTCGGCGGT-
5'

SEQ ID NO 58
5'-GGCGTAATACGACTCACTATAGGCTCTGTAGTTCAGTCGGTAGAACGG
CGGACTTCZAATCCGTATGTCACTGGTTCGAGTCCAGTCAGAGCCGCCA

SEQ ID NO 59
3'-CCGCATTATGCTGAGTGATATCCGAGACATCAAGTCAGCCATCTTGCC
GCCTGAAGPTTAGGCATACAGTGACCAAGCTCAGGTCAGTCTCGGCGGT

01:
SEQ ID NO 60
5'-GGCUCUGUAGUUCAGUCGGUAGAACGGCGGACUUCCAAUCCGUAUGUC
ACUGGUUCGAGUCCAGUCAGAGCCGCCA-3'

02:
SEQ ID NO 61
5'-GGCUCUGUAGUUCAGUCGGUAGAACGGCGGACUPCCAAUCCGUAUGUC
ACUGGUUCGAGUCCAGUCAGAGCCGCCA-3'

03:
SEQ ID NO 62
5'-GGCUCUGUAGUUCAGUCGGUAGAACGGCGGACUUPCAAUCCGUAUGUC
ACUGGUUCGAGUCCAGUCAGAGCCGCCA-3'

04:
SEQ ID NO 63
5'-GGCUCUGUAGUUCAGUCGGUAGAACGGCGGACUUCPAAUCCGUAUGUC
ACUGGUUCGAGUCCAGUCAGAGCCGCCA-3'

05:
SEQ ID NO 64
5'-GGCUCUGUAGUUCAGUCGGUAGAACGGCGGACUZCCAAUCCGUAUGUC
ACUGGUUCGAGUCCAGUCAGAGCCGCCA-3'

-continued

06:

SEQ ID NO 65
5'-GGCUCUGUAGUUCAGUCGGUAGAACGGCGGACUUZCAAUCCGUAUGUC
ACUGGUUCGAGUCCAGUCAGAGCCGCCA-3'

07:

SEQ ID NO 66
5'-GGCUCUGUAGUUCAGUCGGUAGAACGGCGGACUUCZAAUCCGUAUGUC
ACUGGUUCGAGUCCAGUCAGAGCCGCCA-3'

Example 6

Synthesis of Tricyclic Analog of
7-deazaisoguanosine and its Triphosphate (FIG. 12)

2-Amino-3,7-dihydro-pyrrolo[2,3-d]pyrimidin-4-one (2).

2,4-Diamino-6-hydroxypyrimidine (25.2 g, 200 mmol) was dissolved in DMF (480 mL) and water (80 mL) at room temperature. Sodium acetate (16.6 g, 200 mmol) was added to this solution and the resulting yellow solution was stirred for 1 h. Chloroacetaldehyde (25.3 mL, 200 mmol) was added, and the mixture was stirred for 46 h at room temperature. The reaction mixture was then concentrated by rotary evaporation. The product was triturated with water (20 mL) and recovered by filtration. The filtered solid was digested in refluxing methanol (500 mL) for 2 h, and the mixture was then placed in a refrigerator at 4° C. overnight to yield a product as a precipitate, which was recovered by filtration, washed with EtOAc (4×250 mL) and dried in a vacuum desiccator over $P_2O_5$ (20 g, 133 mmol, 66% yield).

$^1$H NMR (300 MHz, DMSO-d6) ppm 11 (s, 1H), 10.35 (s, 1H), 6.6 (s, 1H), 6.15 (s, 1H), 6.09 (s, 2H)

N-(4-oxo-4,7-dihydro-3H-pyrrolo[2,3-d]pyrimidin-2-yl) pivalamide (3).

A solution of 2-amino-3,7-dihydro-pyrrolo[2,3-d]pyrimidin-4-one (25 g, 166.66 mmol) in pyridine (300 mL) was treated with trimethylacetyl chloride (65.74 mL, 533 mmol) at 90° C. for 2 h, to give a mixture of N(2)-monoacylated and N(2), N(7)-bisacylated material. The solvent was evaporated and the residue was taken up in aqueous ammonia (28% $NH_3$, 42 mL) and MeOH (300 mL), and stirred at room temperature for 30 min, to selectively cleave the N(7)-pivaloyl group. The product precipitates, and the solid was collected by filtration, washed with cold MeOH, and dried on high vacuum (16 g, 68 mmol, 41% yield).

$^1$H NMR (300 MHz, DMSO-d6) ppm 11.82 (s, 1H), 11.58 (s, 1H), 10.8 (s., 1H), 6.9 (d, J=3.4 Hz, 1H), 6.38 (d, J=3.6 Hz, 1H), 1.2 (s, 9H)

N-(4-chloro-7H-pyrrolo[2,3-d]pyrimidin-2-yl)pivalamide (4).

A mixture of N-(4-oxo-4,7-dihydro-3H-pyrrolo[2,3-d]pyrimidin-2-yl) pivalamide (11 g, 47 mmol), $POCl_3$ (26 mL, 282 mmol), benzyltriethylammonium chloride (21.4 g, 94 mmol), N,N-dimethylaniline (12 mL, 94 mmol), and acetonitrile (104 mL) was heated at reflux for 1 h. The volatiles were removed by rotary evaporation, and the residual oil was slowly added to 800 mL of ice-water (which destroys the remaining $POCl_3$). The pH was adjusted to 4 by dropwise addition of 28% aqueous $NH_4OH$ to generate product as a precipitate, which was collected by filtration, washed with cold water, and purified by silica chromatography (30% ethyl acetate/hexane) to give purified product as a white solid (7 g, 0.27 mol, 58% yield).

$^1$H NMR (300 MHz, DMSO-d6) ppm 12.33 (br. s., 1H), 10.04 (s, 1H), 7.52 (d, J=3.57 Hz, 1H), 6.50 (d, J=3.43 Hz, 1H), 1.20 (s, 9H)

4-Chloro-5-iodo-2-pivaloylamino-7H-pyrrolo[2,3-d]pyrimidine (5)

A solution of compound 4 (5.0 g, 19.84 mmol) and N-Iodosuccinimide (5.35 g, 23.8 mmol) in $CH_2Cl_2$ (100 mL) was stirred at 40° C. for 5 h. The yellow solution was evaporated to an amber residue which was crystallized from MeOH to give yellowish crystals (3.5 g).

$^1$H NMR (300 MHz, DMSO-d6) ppm 1.22 (s, 9H), 7.77 (s, 1H), 10.13 (s, 1H), 12.71 (s, 1H).

4-Chloro-7[-2-deoxy-3,5-di-O-(p-toluoyl)-b-D-erythro-pentofuranosyl]-5-iodo-2-pivaloylamino-7H-pyrrolo[2,3-d] pyrimidine (6)

To a suspension of NaH (60% emulsion in oil, 0.767 g, 17.8 mmol) in dry acetonitrile (400 mL) was added 5 (6.7 g, 17.7 mmol) at room temperature. After incubation for 1 h, 2-deoxy-3,5-di-O-(p-toluoyl)-☐-D-erythro-pentofuranosyl chloride (12.1 g, 22.6 mmol) was added to the reaction mixture, which was stirred further for 16 h. The product (5 g) was obtained as a white solid after removal of the solvent on a rotary evaporator and purification by silica gel chromatography (EtOAc/hexanes 1:4).

$^1$H NMR (300 MHz, DMSO-d6) ppm 1.21 (s, 9H), 2.37, 2.39 (2 s, 6H), 2.69-2.75 (m, 1H), 3.19-3.25 (m, 1H), 4.47-4.53 (m, 2H), 4.61-4.67 (m, 1H), 5.77-5.79 (m, 1H), 6.63 (t, 1H, J=6.8 Hz), 7.31, 7.37, 7.84, 7.94 (4 d, 8H, J=8.1 Hz), 7.99 (s, 1H), 10.29 (s, 1H).

7-(2-Deoxy-b-D-erythro-pentofuranosyl)-5-iodo-7H-pyrrolo-[2,3-d]pyrimidine-2,4-diamine (7)

A suspension of compound 6 (3 g, 4.1 mmol) in dioxane (60 mL) and 25% $NH_3/H_2O$ (160 mL) was introduced into an stainless steel pressure bomb and stirred at 120° C. for 24 h. The clear solution was evaporated and the residue was subjected to flash chromatography (silica gel, column, EtOAc:MeOH:$H_2O$, 80:17:3). The main zone was collected and rotavap to a brown color solid of 2 (3 g, 94%). [Seela, F Synthesis 2004, 8, 1203-1210]

$^1$H NMR (300 MHz, DMSO-d6) ppm 7.40 (br. s., 2H), 7.01 (d, J=3.6 Hz, 1H), 6.22-6.38 (m, 3H), 5.22 (d, J=2.9 Hz, 1H), 4.27 (br. s., 1H), 3.75 (br. s., 1H), 3.40-3.56 (m, 2H), 2.27-2.42 (m, 1H), 2.05 (dd, J=12.8, 5.7 Hz, 1H)

2,4-Diamino-5-[(E)-1-(methoxycarbonyl)-2-ethenyl]-7-(2-deoxy-b-D-erythro-pentofuranosyl)pyrrolo[2,3-d]pyrimidine (8)

To a solution of 7 (391 mg, 1.0 mmol) in DMF (10 mL) including Et3N (0.28 mL, 2.0 mmol) and $(PPh_3)_2PdCl_2$ (70 mg, 0.1 mmol) was added methyl acrylate (3.62 mL, 40 mmol), and the reaction mixture was heated to 70° C. for 5 h. The solvent was removed in vacuum, and the residue was purified by flash chromatography (silica gel, column, EtOAc:MeOH:$H_2O$, 80:17:3). The main zone was collected and rotavap to a brown color solid of 3 (200 mg).

$^1$HNMR (300 MHz, DMSO-d6) ppm 7.82 (d, 1H, J=15.5 Hz), 7.71 (s, 1H), 6.36 (dd, 1H, J=5.7 and 8.3 Hz), 6.36 (br s, 2H), 6.30 (d, 1H, J=15.5 Hz), 5.82 (br s, 2H), 5.22 (d, 1H, J=3.5 Hz), 5.02 (t, 1H, J=5.8 Hz), 4.31 (m, 1H), 3.77 (m, 1H), 3.68 (s, 3H), 3.55 and 3.49 (m, 1H), 2.38 (ddd, 1H, J=8.3, 5.5, and 13.2 Hz), 2.09 (ddd, 1H, J=5.7, 2.9, and 13.2 Hz)

4-Amino-2-(2-deoxy-b-D-erythro-pentofuranosyl)-2,6-dihydro-7H-2,3,5,6-tetraazabenzo[cd]azulen-7-one (9)

A solution of 8 (1.1 g, 3.148 mmol) in 0.1 M NaOMe in MeOH (157 mL) was heated at 70° C. for 12 h. The reaction mixture was cooled to 0° C., and the resulting precipitate was collected to give 9 as yellow solid. The filtrate was removed in vacuo and the residue was purified by silica gel column eluted with MeOH (25%) in DCM to give additional 9 (1.3 g).

¹H NMR (300 MHz, DMSO-d6) ppm 10.08 (d, 1H, J=1.2 Hz), 7.34 (s, 1H), 6.93 (d, 1H, J=12.0 Hz), 6.29 (dd, 1H, J=5.9 and 7.9 Hz), 6.25 (brs, 2H,), 5.58 (d, 1H, J=11.6 Hz), 5.26 (d, 1H, J=3.6 Hz), 5.02 (t, 1H, J=5.8 Hz), 4.30 (m, 1H), 3.77 (m, 1H), 3.49 (m, 2H), 2.49 (m, Regiosela 1H), 2.12 (ddd, 1H, J=6.1, 2.3, and 12.8 Hz). [Hirama, Y. Biorg & Medic Chem 19, 352-358]

Synthesis of Compound 10

To a stirred solution of compound 9 (100 mg, 0.315 mmol) in 20% AcOH—H$_2$O (v/v, 6 mL), was added dropwise a solution of NaNO$_2$ (45 mg, 0.66 mmol) in H$_2$O (1.0 mL) at r.t. The stirring was continued for 1 h. 50 min, and the pH of the dark solution was adjusted to 8.0 with 25% aq NH$_3$ under cold condition. The solid obtained was filtered and dried (50 mg).

HRMS: [M+H]$^+$=319.1

Synthesis of Compound 11

To a suspension of 10 (425 mg, 1.336 mmol) in dry pyridine (25 mL) were added diphenylcarbamoyl chloride (557 mg, 2.4 mmol) and N,N-diisopropylethylarnine (0.42 mL, 2.4 mmol). The mixture was stirred for 4 h at room temperature, and then poured in the 5% aqueous NaHCO$_3$ (50 mL) and extracted with CH$_2$Cl$_2$ (2×100 mL). The combined CH$_2$Cl$_2$ layers were dried over Na$_2$SO$_4$ and clarified by filtration. The product 11 was then recovered by rotary evaporation and purified by flash chromatography (silica gel, elution with CH$_2$Cl$_2$ followed by CH$_2$Cl$_2$—MeOH step wise from 0 to 4% methanol) to give a brown color foam (350 mg).

HRMS: [M+H]$^+$=514.1721

Synthesis of Compound 12

Compound 11 (350 mg, 0.68 mmol) was dried by co-evaporation with anhydrous pyridine (2×, 15 mL) and dissolved in anhydrous pyridine (25 mL). This solution was treated with dimethoxytrityl chloride (276 g, 0.82 mmol) at room temperature under stirring for 4 h. Water was then added to the mixture and the stirring was continued for 35 min. The mixture was diluted with a 5% aqueous NaHCO$_3$ solution (100 mL) and extracted with CH$_2$Cl$_2$ (2×350 mL). The combined extracts were dried over Na$_2$SO$_4$. The solvent was removed by rotary evaporation, and the product 10 was obtained as an orange-brown foam (400 mg) by purification by flash chromatography (silica gel, eluted with 2:1 to 1:2, hexane:ethyl acetate).

HRMS: [M+Na]$^+$=838.28

Synthesis of Compound 13

12 (0.44 mmol, 400 mg), DMAP (0.25 mmol, 31 mg), Et$_3$N (1.1 mmol, 0.154 mL), and Ac$_2$O (0.528 mmol, 0.049 mL) were added to a solution of dry pyridine (10 mL). The mixture was stirred at room temperature for 2 h. MeOH (1 mL) was added, the mixture was diluted with 100 mL of dichloromethane and extracted with 5% NaHCO$_3$ (50 mL). The aqueous layer was back extracted with dichloromethane (100 mL). The combined organic layers were dried over sodium sulfate, filtered and concentrated by rotary evaporation. The residue was purified by flash chromatography (hexane:ethyl acetate, 2:1 to 1:2) to give product 13 (350 mg).

HRMS: [M+Na]$^+$=880.2953

Synthesis of Compound 14

Compound 13 (350 mg, 0.41 mmol) was dissolved in a mixture (50 mL) of dichloromethane and methanol (7:3). The solution was cooled to 0° C., dichloroacetic acid (0.83 mL, 10.2 mmol) was added, and stirring was continued at 0° C. for 2 h. The mixture was then neutralized with aqueous saturated NaHCO$_3$ (50 mL), and extracted with dichloromethane (100 mL). The resulting organic layer was dried over sodium sulfate, concentrated by rotary evaporation, and the residue was purified by column chromatography (hexane:ethyl acetate 1:2 to 0:1) to give product as a white solid (155 mg).

HRMS: [M+H]$^+$=556.1827

Synthesis of Compound 15

To a solution of compound 14 (0.155 g, 0.28 mmol) in pyridine (5 mL) and dioxane (10 mL) was added a solution of 2-chloro-4-H-1,3,2-benzodioxaphosphorin-4-one (0.085 g, 0.42 mmol) in dioxane (5.0 mL) at room temperature. After incubation for 15 min, a mixture of tributylammonium pyrophosphate in DMF (0.2 M, 4.2 mL, 0.84 mmol) and tributylamine (0.45 mL) was added. After incubating for 20 min, a solution of iodine (0.1064 g, 0.42 mmol) and water (0.315 mL) in pyridine (15.5 mL) was added. After incubating for 30 min, the reaction was quenched by the addition of aqueous Na$_2$SO$_3$ (5%, until color disappears). The pyridine and dioxane were removed by rotary evaporation. The residue was dissolved in a mixture of water and acetonitrile (10 mL each) and kept at room temperature overnight. The product was resolved by reverse phase preparative LC (gradient 25 mM TEAA to 25 mM TEAA:CH$_3$CN (1:1)=5:95 in 38 min, running time 46 min), with the solvents in the fraction containing the product removed by lyophilization. The residue was dissolved in ammonium hydroxide (2 mL), and the solution was stirred at room temperature for 3 h. The solution was injected onto an ion exchange HPLC column. The product (14 mg) was recovered as a yellow solid by lyophilization of fractions collected by gradient elution (water to 1 M ammonium bicarbonate over 32 min; running time 42 min)

HRMS: [M−H]$^-$=556.9881

What is claimed is:

1. A process for increasing the number of copies of an oligonucleotide having an initial oligonucleotide sequence, wherein said oligonucleotide contains one or more non-standard nucleotides that carry a heterocycle selected from the group consisting of wherein R is the point of attachment of said heterocycle to the 2'-deoxyribose backbone in said chain, said process comprising:

(a) dissolving said oligonucleotide in an aqueous mixture containing a thermostable DNA polymerase, nucleoside triphosphates that are Watson-Crick complementary to the nucleotides in said oligonucleotide, a first oligonucleotide primer that is sufficiently complementary to a segment at or near the 3'-end of said oligonucleotide that it hybridizes to said oligonucleotide, and a second oligonucleotide primer that has a sequence substantially identical to a portion of said oligonucleotide at or near its 5'-end, (b) incubating said mixture at a temperature where said polymerase extends the first oligonucleotide primer to give an extension product that is substantially complementary to said oligonucleotide, wherein said extension product forms a duplex with said oligonucleotide, such that said extension product, when it is separated from said oligonucleotide, can hybridize with the second primer, (c) then increasing the temperature of said mixture to a temperature sufficient to separate said oligonucleotide from said extension product, (d) then lowering the temperature of said mixture to a temperature at which the first oligonucleotide primer can hybridize to said oligonucleotide and the second oligonucleotide primer can hybridize to said extension product, and (e) repeating steps (b) through (d).

2. A process for increasing the number of copies of an oligonucleotide having an initial oligonucleotide sequence, wherein said oligonucleotide contains one or more nonstandard nucleotides that carry a heterocycle selected from the group consisting of

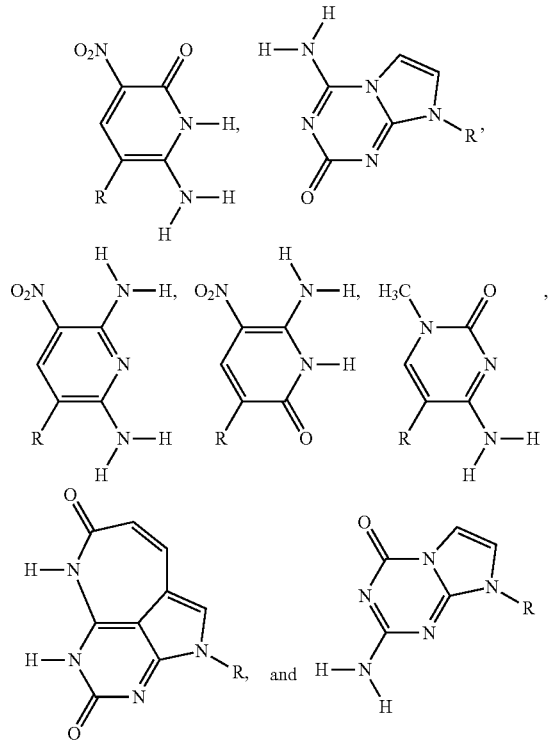

wherein R is the point of attachment of said heterocycle to the 2'-deoxyribose backbone in said chain, said process comprising:

(a) dissolving said oligonucleotide in an aqueous mixture containing a thermostable DNA polymerase, nucleoside triphosphates that are Watson-Crick complementary to the nucleotides in said oligonucleotide, a first oligonucleotide primer that is sufficiently complementary to a segment at or near the 3'-end of said oligonucleotide that it hybridizes to said oligonucleotide, and a second oligonucleotide primer that has a sequence substantially identical to a portion of said oligonucleotide at or near its 5'-end, (b) incubating said mixture at a temperature where said polymerase extends the first oligonucleotide primer to give an extension product that is substantially complementary to said oligonucleotide, wherein said extension product forms a duplex with said oligonucleotide, such that said extension product, when it is separated from said oligonucleotide, can hybridize with the second primer, (c) then increasing the temperature of said mixture to a temperature sufficient to separate said oligonucleotide from said extension product, (d) then lowering the temperature of said mixture to a temperature at which the first oligonucleotide primer can hybridize to said oligonucleotide and the second oligonucleotide primer can hybridize to said extension product, and (e) repeating steps (b) through (d).

3. The process of claim 2, wherein said oligonucleotide contains a nucleotide having the heterocycle,

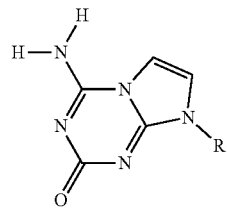

and the mixture contains a nucleoside triphosphate having the heterocycle

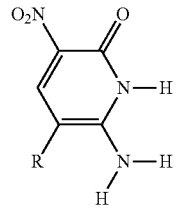

wherein each R is the point of attachment of the heterocycle to the 2'-deoxyribose of the nucleotides and nucleoside triphosphates.

4. The process of claim 2, wherein said oligonucleotide contains a nucleotide having the heterocycle,

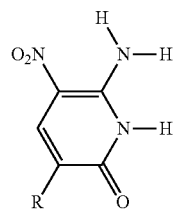

and the mixture contains a nucleoside triphosphate having the heterocycle

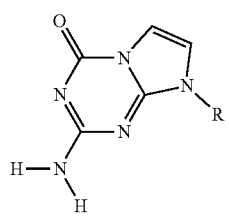

wherein each R is the point of attachment of the heterocycle to the 2'-deoxyribose of the nucleotides and nucleoside triphosphates.

5. The process of claim 2, wherein said oligonucleotide contains a nucleotide having the heterocycle,

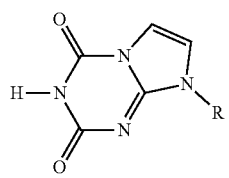

and the mixture contains a nucleoside triphosphate having the heterocycle

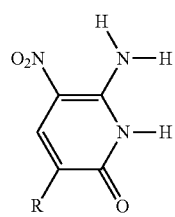

wherein each R is the point of attachment of the heterocycle to the 2'-deoxyribose of the nucleotides and nucleoside triphosphates.

6. The process of claim 1, wherein said oligonucleotide contains a nucleotide having the heterocycle,

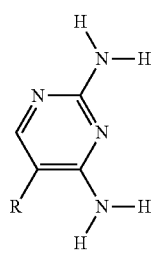

and the mixture contains a nucleoside triphosphate having the heterocycle

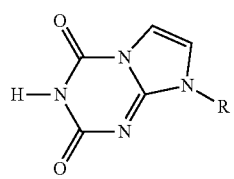

wherein each R is the point of attachment of the heterocycle to the 2'-deoxyribose of the nucleotides and nucleoside triphosphates.

7. The process of claim 1, wherein said oligonucleotide contains a nucleotide having the heterocycle,

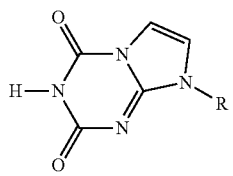

and the mixture contains a nucleoside triphosphate having the heterocycle

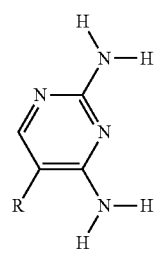

wherein each R is the point of attachment of the heterocycle to the 2'-deoxyribose of the nucleotides and nucleoside triphosphates.

8. The process of claim 2, wherein said oligonucleotide contains a nucleotide having the heterocycle,

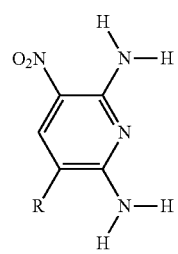

and the mixture contains a nucleoside triphosphate having the heterocycle

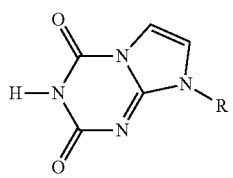

wherein each R is the point of attachment of the heterocycle to the 2'-deoxyribose of the nucleotides and nucleoside triphosphates.

9. The process of claim 2, wherein said oligonucleotide contains a nucleotide having the heterocycle,

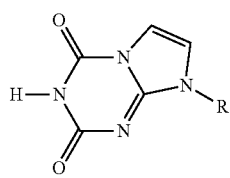

and the mixture contains a nucleoside triphosphate having the heterocycle

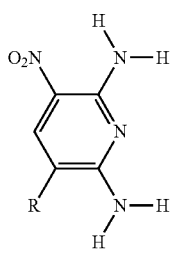

wherein each R is the point of attachment of the heterocycle to the 2'-deoxyribose of the nucleotides and nucleoside triphosphates.

10. The process of claim 1, wherein said oligonucleotide contains a nucleotide having the heterocycle,

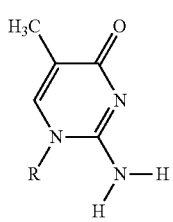

and the mixture contains a nucleoside triphosphate having the heterocycle

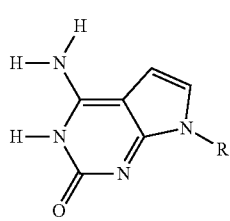

wherein each R is the point of attachment of the heterocycle to the 2'-deoxyribose of the nucleotides and nucleoside triphosphates.

11. The process of claim 1, wherein said oligonuleotide contains a nucleotide having the heterocycle,

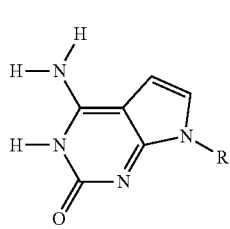

and the mixture contains a nucleoside triphosphate having the heterocycle

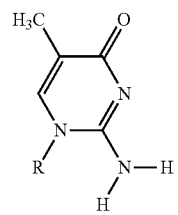

wherein each R is the point of attachment of the heterocycle to the 2'-deoxyribose of the nucleotides and nucleoside triphosphates.

12. The process of claim 1, wherein said oligonucleotide contains a nucleotide having the heterocycle,

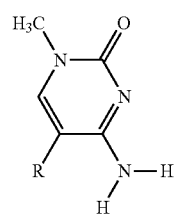

and the mixture contains a nucleoside triphosphate having the heterocycle

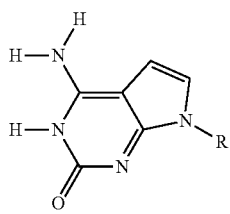

wherein each R is the point of attachment of the heterocycle to the 2'-deoxyribose of the nucleotides and nucleoside triphosphates.

13. The process of claim 1, wherein said oligonucleotide contains a nucleotide having the heterocycle,

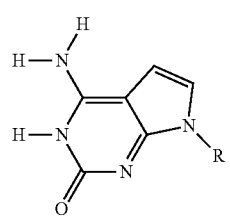

and the mixture contains a nucleoside triphosphate having the heterocycle

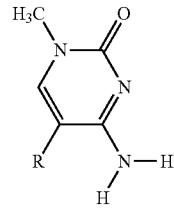

wherein each R is the point of attachment of the heterocycle to the 2'-deoxyribose of the nucleotides and nucleoside triphosphates.

14. The process of claim 1, wherein said oligonucleotide contains a nucleotide having the heterocycle,

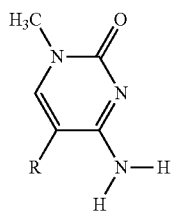

and the mixture contains a nucleoside triphosphate having the heterocycle

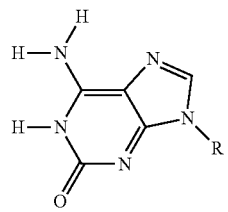

wherein each R is the point of attachment of the heterocycle to the 2'-deoxyribose of the nucleotides and nucleoside triphosphates.

15. The process of claim 1, wherein said oligonucleotide contains a nucleotide having the heterocycle,

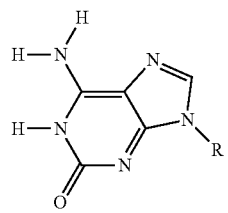

and the mixture contains a nucleoside triphosphate having the heterocycle

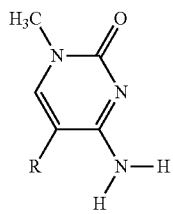

wherein each R is the point of attachment of the heterocycle to the 2'-deoxyribose of the nucleotides and nucleoside triphosphates.

16. The process of claim 2, wherein said oligonucleotide contains a nucleotide having the heterocycle,

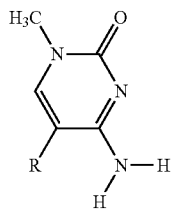

and the mixture contains a nucleoside triphosphate having the heterocycle

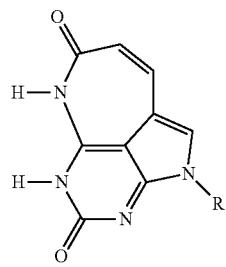

wherein each R is the point of attachment of the heterocycle to the 2'-deoxyribose of the nucleotides and nucleoside triphosphates.

17. The process of claim 2, wherein said oligonucleotide contains a nucleotide having the heterocycle,

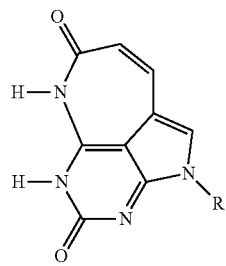

and the mixture contains a nucleoside triphosphate having the heterocycle

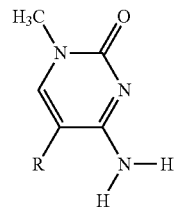

wherein each R is the point of attachment of the heterocycle to the 2'-deoxyribose of the nucleotides and nucleoside triphosphates.

18. The process of claim 2, wherein said oligonucleotide contains a nucleotide having the heterocycle,

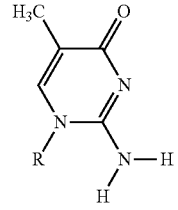

and the mixture contains a nucleoside triphosphate having the heterocycle

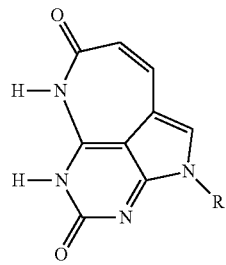

wherein each R is the point of attachment of the heterocycle to the 2'-deoxyribose of the nucleotides and nucleoside triphosphates.

19. The process of claim 2, wherein said oligonucleotide contains a nucleotide having the heterocycle,

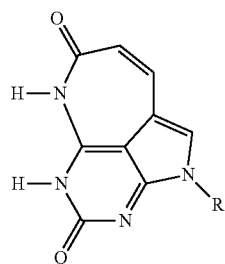

and the mixture contains a nucleoside triphosphate having the heterocycle

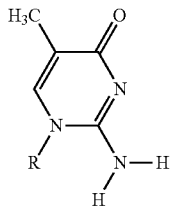

wherein each R is the point of attachment of the heterocycle to the 2'-deoxyribose of the nucleotides and nucleoside triphosphates.

20. The process of claim 1, wherein at least 95% of the non-standard nucleotide is retained within the product to at least 95% for each cycle of extension of the first primer, separation by heating, and extension of the second primer.

21. The process of claim 7, wherein said polymerase is a variant of the DNA polymerase 1 from *Thermus aquaticus*.

22. The process of claim 8, wherein said polymerase is a variant of the DNA polymerase 1 from *Thermus aquaticus*.

23. A kit that allows the practice of the process in claim 1, wherein said kit contains nucleoside triphosphates, wherein one or more of said nucleoside triphosphates carries a heterocycle selected from the group consisting of

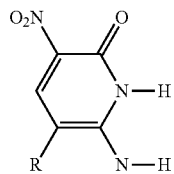
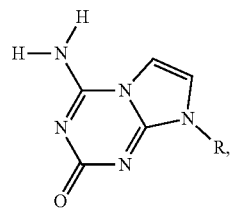
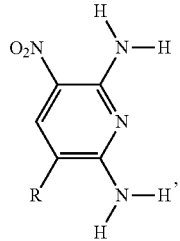
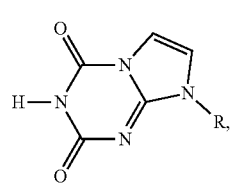

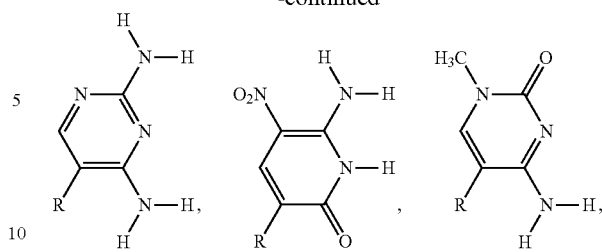

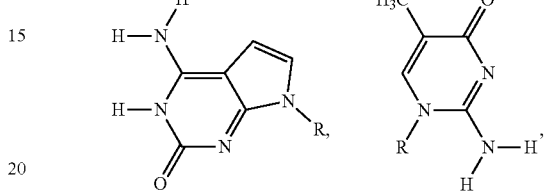

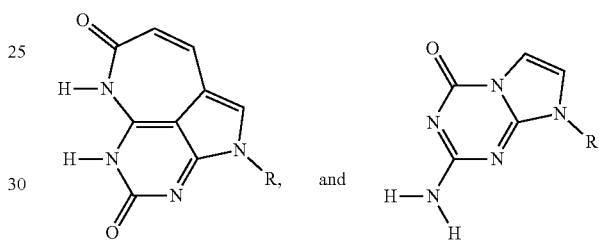

and a polymerase that incorporates said triphosphate opposite its Watson-Crick complement in a template.

24. The process of claim 2, wherein said oligonucleotide contains a nucleotide having the heterocycle,

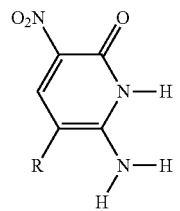

and the mixture contains a nucleoside triphosphate having the heterocycle

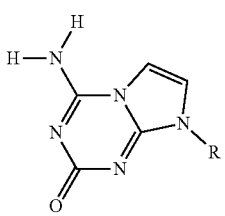

wherein each R is the point of attachment of the heterocycle to the 2'-deoxyribose of the nucleotides and nucleoside triphosphates.

25. The process of claim 2, wherein at least 95% of the non-standard nucleotide is retained within the product to at least 95% for each cycle of extension of the first primer, separation by heating, and extension of the second primer.

26. A kit that allows the practice of the process in claim 2, wherein said kit contains nucleoside triphosphates, wherein one or more of said nucleoside triphosphates carries a heterocycle selected from the group consisting of

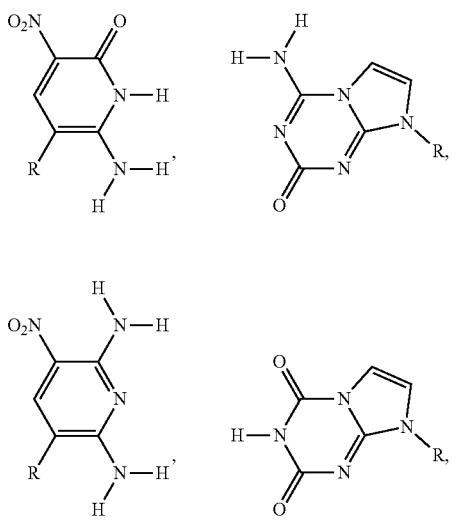

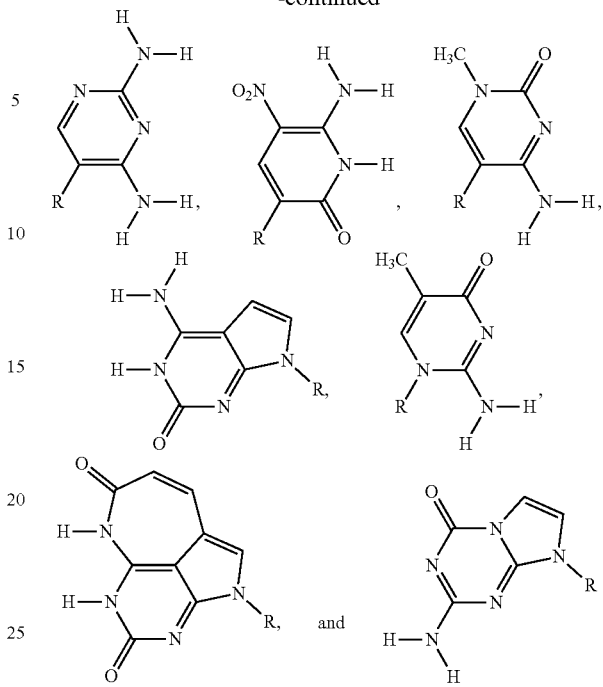

and a polymerase that incorporates said triphosphate opposite its Watson-Crick complement in a template.

* * * * *